US008870911B2

(12) United States Patent
Williams et al.

(10) Patent No.: US 8,870,911 B2
(45) Date of Patent: Oct. 28, 2014

(54) FORCEPS COMPRISING A TROCAR TIP

(75) Inventors: Norman Stanley Williams, London (GB); Zhiqiang Weng, Sheung Wan (HK)

(73) Assignees: Queen Mary & Westfield College, London (GB); Frankenman International Limited, Sheung Wan (HK)

( * ) Notice: Subject to any disclaimer, the term of this patent is extended or adjusted under 35 U.S.C. 154(b) by 274 days.

(21) Appl. No.: 13/228,542

(22) Filed: Sep. 9, 2011

(65) Prior Publication Data

US 2012/0065665 A1 Mar. 15, 2012

Related U.S. Application Data

(60) Provisional application No. 61/452,194, filed on Mar. 14, 2011.

(30) Foreign Application Priority Data

Sep. 9, 2010 (WO) ................ PCT/CN2010/076755

(51) Int. Cl.
*A61B 17/00* (2006.01)
*A61B 17/34* (2006.01)
*A61B 17/115* (2006.01)
*A61B 17/29* (2006.01)
*A61B 17/02* (2006.01)

(52) U.S. Cl.
CPC ........... *A61B 17/115* (2013.01); *A61B 17/1155* (2013.01); *A61B 2017/2926* (2013.01); *A61B 17/29* (2013.01); *A61B 17/02* (2013.01); *A61B 17/3417* (2013.01); *A61B 2017/00353* (2013.01)
USPC ............................ 606/205; 606/185; 606/219

(58) Field of Classification Search
USPC ............. 606/49–52, 153–156, 169, 174, 185, 606/205–211, 219; 604/164.01; 227/175.1–182.1
See application file for complete search history.

(56) References Cited

U.S. PATENT DOCUMENTS 3,895,636 A  7/1975 Schmidt
4,576,167 A  3/1986 Noiles
(Continued)

FOREIGN PATENT DOCUMENTS

CN  1252255 A  5/2000
CN  2448296 Y  9/2001
(Continued)

OTHER PUBLICATIONS

Keighley, M.R.B. & Williams, N. S., Surgery of the Anus Rectum and Colon, 3rd Ed., Saunders Ltd., 2008: Chapter 5, pp. 175-278.
(Continued)

*Primary Examiner* — Thomas McEvoy
(74) *Attorney, Agent, or Firm* — Pepper Hamilton LLP

(57) ABSTRACT

The present invention relates to a forceps comprising an elongate body, a grip region at end of the elongate body, the grip region comprising a lever, a grasping assembly at the opposite end of the elongate body, the grasping assembly comprising a movable grasper and a trocar, and an actuating mechanism coupling the lever to the grasping assembly for effecting movement of the grasper relative to the elongate body. The present invention also relates to a kit of parts comprising a forceps of the invention and additional components. The invention further relates to a method of forming an anastomosis between two surfaces and a method of forming a stoma trephine in a subject using the kit of parts of the invention. The present invention also relates to the use of the forceps and the kit or parts of the invention in such methods.

5 Claims, 28 Drawing Sheets

(56) References Cited

U.S. PATENT DOCUMENTS

| | | | |
|---|---|---|---|
| 5,318,040 A | 6/1994 | Kensey et al. | |
| 5,325,866 A | 7/1994 | Krzyzanowski | |
| 5,535,754 A | 7/1996 | Doherty | |
| 5,669,918 A * | 9/1997 | Balazs et al. | 606/139 |
| 5,758,814 A | 6/1998 | Gallagher et al. | |
| 6,053,933 A | 4/2000 | Balazs et al. | |
| 7,318,830 B2 | 1/2008 | Mayoral | |
| 7,401,722 B2 | 7/2008 | Hur | |
| 7,422,138 B2 | 9/2008 | Bilotti et al. | |
| 7,547,312 B2 | 6/2009 | Bauman et al. | |
| 8,181,838 B2 | 5/2012 | Milliman et al. | |
| 8,231,042 B2 | 7/2012 | Hessler et al. | |
| 8,393,516 B2 | 3/2013 | Kostrzewski | |
| 8,485,414 B2 | 7/2013 | Criscuolo et al. | |
| 8,496,157 B2 | 7/2013 | Olson | |
| 8,684,251 B2 | 4/2014 | Rebuffat et al. | |
| 8,684,254 B2 | 4/2014 | Kostrzewski | |
| 8,733,611 B2 | 5/2014 | Milliman | |
| 2003/0236529 A1 | 12/2003 | Shluzas et al. | |
| 2004/0217146 A1 | 11/2004 | Beck | |
| 2005/0023325 A1 | 2/2005 | Gresham et al. | |
| 2006/0155326 A1 | 7/2006 | Aranyi | |
| 2010/0096435 A1 | 4/2010 | Fuchs et al. | |
| 2011/0095067 A1 * | 4/2011 | Ohdaira | 227/175.2 |

FOREIGN PATENT DOCUMENTS

| | | |
|---|---|---|
| CN | 2492196 Y | 5/2002 |
| CN | 101011277 A | 8/2007 |
| EP | 0074878 A2 | 3/1983 |
| EP | 0536882 A2 | 4/1993 |
| EP | 0908150 A2 | 4/1999 |
| EP | 2153781 A2 | 2/2010 |
| EP | 2184018 A2 | 5/2010 |
| JP | 2009291492 A | 12/2009 |
| WO | 01/66020 A2 | 9/2001 |
| WO | 2004/089255 A1 | 10/2004 |
| WO | 2006/075153 A1 | 7/2006 |
| WO | 2007/121238 A2 | 10/2007 |
| WO | 2008/101497 A1 | 8/2008 |
| WO | 2009/137761 A2 | 11/2009 |

OTHER PUBLICATIONS

Williams, N. S., et al., EXternal Pelvic REctal SuSpension (Express procedure) for rectal intussusception, with and without rectocele repair, Br. J. Surg., May 2005;92(5):598-604.

Williams, N. S., et al., Anterior Perineal PlanE for Ultra-low Anterior Resection of the Rectum (the APPEAR technique): a prospective clinical trial of a new procedure, Ann Surg., May 2008;247(5):750-758.

Single Use Curved Intraluminal Circular Stapler, Product Brochure, Frankenman International Limited (obtained from website http://www.frankenman.com prior to the priority date of the current application).

El-Gendy, K. A., et al, Anterior Perineal PlanE for Ultralow Anterior Resection of the Rectum (the APPEAR Technique): a video demonstration, Ann Surg Oncol. May 2010;17(5):1357-8. Epub Dec. 29, 2009.

Fazio, V., W., Rob and Smith's Operative Surgery: Alimentary tract and abdominal wall: Colon, Rectum and Anus, 4th edition, 1983, pp. 54-62 & 91-93, published by Butterworths and edited by Ian P. Todd and L. P. Fielding.

Official Action dated Jun. 25, 2014 issued in related U.S. Appl. No. 13/228,729.

* cited by examiner

FORCEPS COMPRISING A TROCAR TIP

CROSS-REFERENCE TO RELATED APPLICATIONS

This application claims priority to U.S. provisional application Ser. No. 61/452,194 filed Mar. 14, 2011 and to International Application No. PCT/CN2010/076755 filed Sep. 9, 2010, each of which is incorporated herein by reference in its entirety.

FIELD OF THE INVENTION

The present invention relates to surgical forceps comprising a trocar tip.

BACKGROUND OF THE INVENTION

Forceps are commonly used during surgery and allow the manipulation of tissue without requiring the surgeon to use their hands to directly manipulate the tissue. Forceps also allow manipulation of tissue that is inaccessible by other means.

Forceps are generally adapted to best serve a particular function. Types of forceps known in the art include artery forceps, haemostatic forceps, dressing forceps, splinter forceps, obstetrical forceps, tubing forceps and tissue forceps. In some surgical techniques, forceps are used to manipulate not just tissue but also other surgical instruments. Forceps may also be used to clamp a tissue, for example an artery, during surgery, to grasp suture needles without causing damage, to assist in the delivery of a baby, or may be used in laparoscopic surgery. An example of forceps used in laparoscopic surgery includes those described in WO 2006/075153, the content of which is hereby incorporated by reference.

Traditional forceps are usually hinged, either at one end or in the middle of the forceps. Forceps can also be either non-locking or locking. Non-locking forceps are also referred to as thumb forceps and can be hinged at the end or in the middle. Examples of non-locking forceps hinged at the end include those described in WO 2007/121238, the content of which is hereby incorporated by reference. Locking forceps are usually hinged in the middle. Some types of forceps are hinged near the grasping end (the grasping end being the end of the forceps that engages with the tissue or surgical instrument to be manipulated).

The part of the forceps that is used to grasp the tissue, surgical instrument or other material often consists of two flat blunt blades which can grasp the object without causing damage. Alternatively the grasping end of the forceps may be adapted according to their particular use, for example taking biopsies of tissue. Examples of this type of forceps include those described in WO 2008/101497, the content of which is hereby incorporated by reference.

A trocar is a sharp surgical instrument that is used to pierce tissues. Trocars are often used in conjunction with cannulae (tubes) as a way of introducing an opening into a tissue or organ, for example into a vein for the administration of intravenous medication. Trocars may also be used to relieve a build up of pressure inside a tissue.

Trocars may be adapted to interact with other surgical instruments. For example, WO 2009/137761 describes a trocar needle, the penetrating tip of the trocar being at the distal end portion and the proximal end portion being insertable into the anvil part of a surgical stapler, for example a circular anastomosis stapler apparatus.

End-to-end anastomosis surgical staplers are used to connect together biological tissues, for example following resection. These staplers can be used to reattach two pieces of bowel following the removal of a diseased portion. The first part of the bowel is attached to an anvil. The anvil is then docked onto the stapler part of the stapler apparatus and positioned such that when the stapler is activated, the two pieces of bowel become reattached with one or more rows of staples in a circular arrangement.

Staplers have also been used in stoma formation. A stoma is an artificial opening between two hollow organs or between one hollow organ and the outside of the body, constructed to permit the passage of body fluids or waste products.

Example surgical staplers include those described in WO 2004/089255 and U.S. Pat. No. 4,576,167.

However, docking of the anvil onto the stapler can be difficult, since the anvil is generally inside a patient's abdomen. This makes manipulation of the anvil problematic, particularly in laparoscopic approaches where entry points into a patient's body are minimal. As a result, several incisions are usually required in order to gain access to the relevant parts of the patient's anatomy. In addition, the use of several different devices is often required to ensure docking of the anvil onto the stapler, and unnecessary damage may be caused to the patient when attempting to dock a stapler anvil onto a stapler. It is also impossible for the surgeon to visualise the docking of the anvil onto the stapler since docking usually occurs inside the patient.

Accordingly, there remains in the art a need for a surgical device that enables manipulation of other surgical devices, such as surgical stapler anvils, whilst reducing damage caused to surrounding tissue and reducing the number of surgical devices that need to be used at once.

SUMMARY OF THE INVENTION

The inventors have developed a forceps which includes a trocar tip. The trocar tip can be used to penetrate tissues and subsequently the forceps can be used to retrieve the anvil of a surgical stapler apparatus. In particular the forceps can be adapted to be insertable into the anvil of a surgical circular stapler apparatus and be used to retrieve an anvil from a patient ready for docking onto a stapler.

Accordingly, the present invention relates to a forceps comprising:
(a) an elongate body;
(b) a grip region at one end of the elongate body, the grip region comprising a lever;
(c) a grasping assembly at the opposite end of the elongate body, the grasping assembly comprising a movable grasper and a trocar; and
(d) an actuating mechanism coupling the grip region to the grasping assembly for effecting movement of the grasper relative to the elongate body.

The present invention also relates to a kit of parts comprising a forceps according to the invention and a surgical stapler apparatus.

The present invention also relates to a method of forming an anastomosis in a subject using the kit of parts of the invention.

The present invention also relates to a method of forming a stoma trephine in a subject using the kit of parts of the invention.

The present invention further relates to the use of the forceps of the invention in the formation of an anastomosis or stoma trephine.

The present invention further relates to the use of the kit of parts of the invention in the formation of anastomosis or stoma trephine.

DETAILED DESCRIPTION

Figure 1:
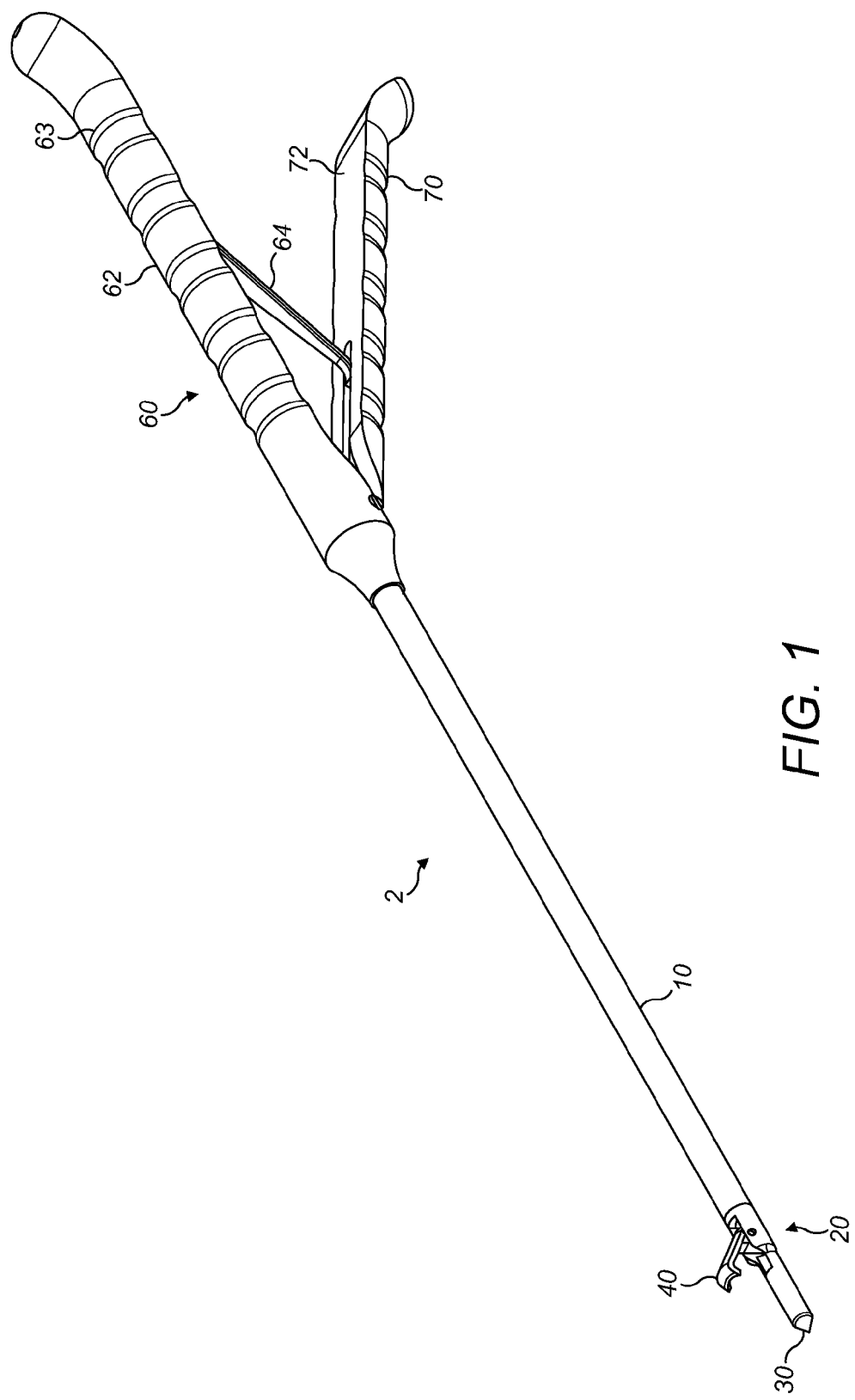
FIG. 1 is a perspective view of the adapted forceps of the invention.
Figure 2:
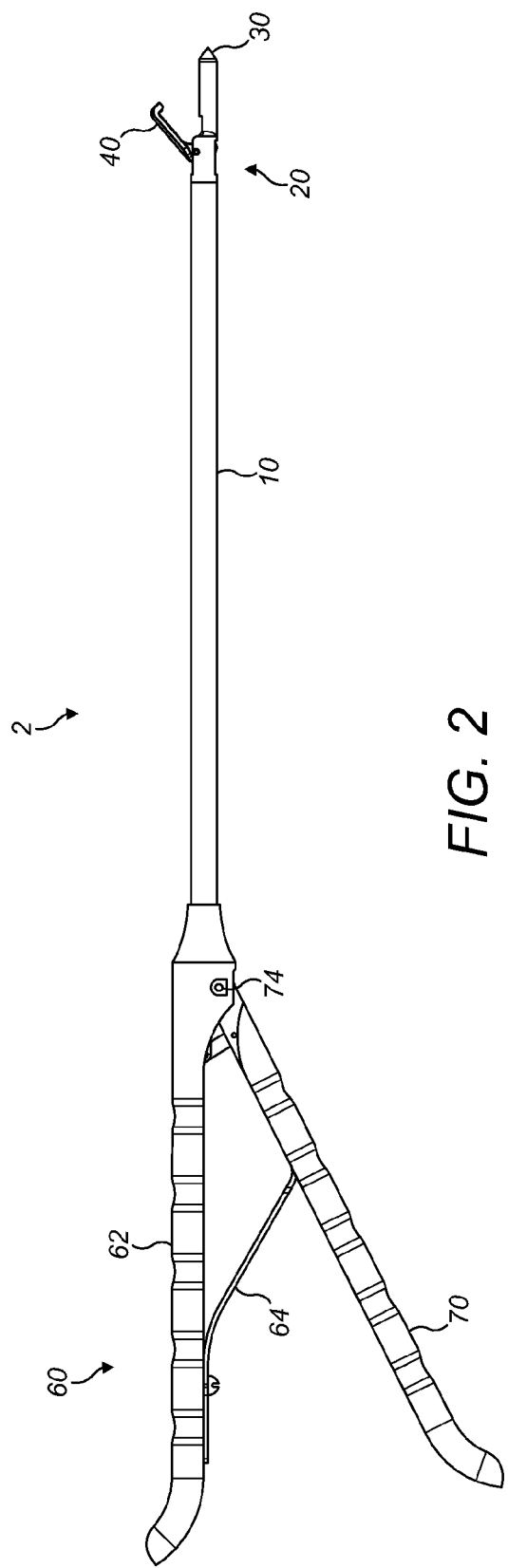
FIG. 2 is a side view of the adapted forceps of the invention.
Figure 3:
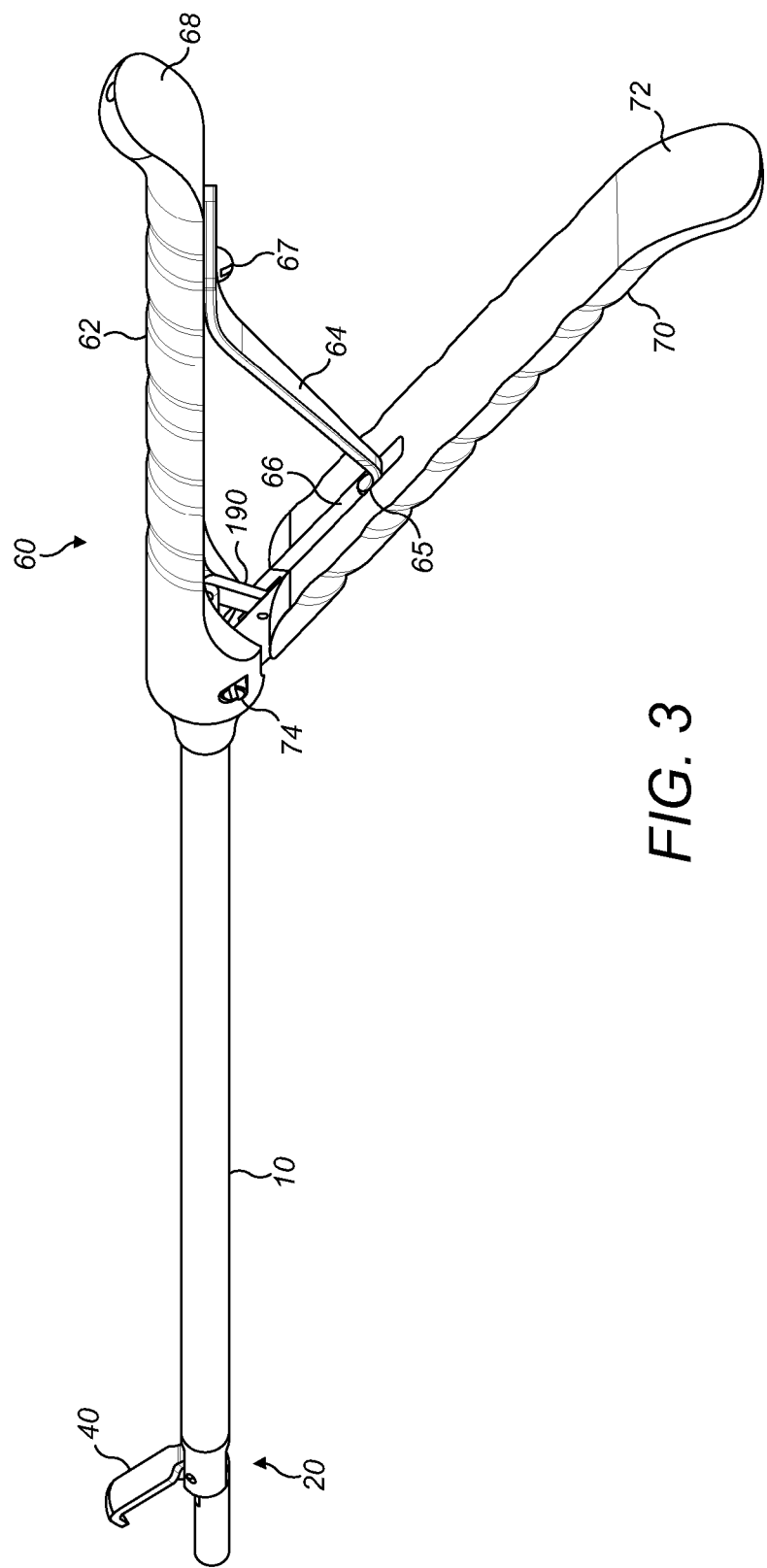
FIG. 3 is a perspective view from the rear of the adapted forceps of the invention.

Referring to FIGS. 1 to 3, in a first aspect of the invention, there is provided a forceps 2 comprising:

(a) an elongate body 10;

(b) a grip region 60 at one end of the elongate body, the grip region comprising a lever 70;

(c) a grasping assembly 20 at the opposite end of the elongate body, the grasping assembly comprising a movable grasper 40 and a trocar 30; and (c) an actuating mechanism coupling the grip region to the grasping assembly for effecting movement of grasper relative to the elongate body.

The elongate body can be any length which is suitable for the particular purpose of the forceps. In some embodiments, the length of the elongate body is between 5 and 50 cm in length, preferably between 10 and 30 cm in length. In some embodiments the elongate body is straight, although the elongate body can be curved or bent according to requirements. If the elongate body is curved, the grasping assembly and/or the trocar can be arranged to continue the curve of the elongate body.

The elongate body is cylindrical or substantially cylindrical in cross section. This includes circular and ovoid cross sections as well as suitable polygonal cross sections, for example triangular, square, pentagonal, hexagonal, heptagonal, octagonal, nonagonal, decagonal and so on.

The grip region 60 can also be said to be a gripping assembly and is intended to be the section of the forceps that is held by the user. Optionally the grip region includes indentations or grooves 63 which increase the coefficient of friction between the forceps and the user's hand and hence make the forceps easier to grip firmly. The indentations or grooves also therefore reduce the risk of the forceps being dropped accidentally. The grip region 60 can be attached to or integral with the elongate body.

In preferred embodiment, the grip region comprises a lever 70 and a handle 62 as shown in FIG. 1. Either or both of the lever 70 and handle 62 may include indentations or grooves 63 to aid gripping. Preferably the handle and the lever are so arranged to allow the user to activate the lever whilst holding the forceps by the handle. Activation of the forceps involves pivotal movement of the lever towards the handle.

The handle can be integral with the elongate body and so may be considered an extension of the elongate body. In some embodiments, the handle is substantially parallel to the elongate body and may be aligned coaxially with the elongate body. Alternatively, the handle may form an angle with the elongate body, for example between 0° and 90° or between 0° and 45° or between 10° and 45°.

The lever has an open position and a closed position. FIGS. 1 and 2 show the lever in the open position. As shown in FIG. 2, the lever can be attached to the handle by a pin 74 forming the pivot of the lever. Alternatively, the lever can be attached to the elongate body by a similar pin forming the pivot of the lever. To enable the lever to be fully closed against the handle, the lever and the handle optionally comprise a pair of opposing substantially planar sides 68 and 72, as shown in FIG. 3, such that when the lever is closed, the two planar sides move towards each other and eventually are pressed together. The opposite sides of each of the lever and the handle are usually curved to provide an ergonomic gripping region for the user.

The grip region may optionally include a resilient bias 64 which maintains the lever in the open position. The resilient bias is also known as a resilient biasing means. The resilient bias can be any suitable resilient bias known to a person of skill in the art, for example a spring or, as shown in FIG. 3, a flexible member attached at one end to the planar side of the handle 68, for example by means of a bolt 67. The opposite end of the flexible member presses against the opposing planar surface 72 of the lever 70 to urge it into the open position.

In some embodiments, the flexible member comprises a flange 65 that presses against the planar surface 72 of the lever 70. In another embodiment, the planar surface 72 of the lever 70 may contain a channel 66 that receives the flange 65 as shown in FIG. 3 and guides the flexible member along the planar surface 72 of the lever 70 as the forceps are closed by a user.

Figure 4:
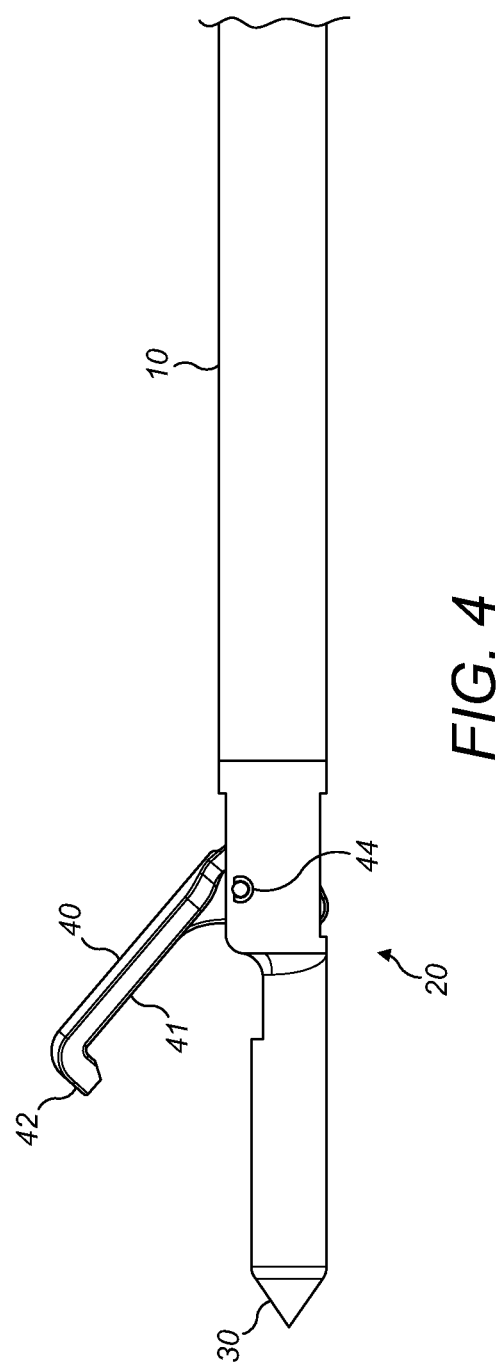
FIG. 4 is a close up side-on view of the grasping region of the adapted forceps of the invention.

Referring to FIG. 4, the grasping assembly 20 of the forceps 2 of the invention comprises a trocar 30 and a movable grasper 40. In a preferred embodiment, the grasping assembly 20 is aligned coaxially or substantially coaxially with the elongate body. In another embodiment, the trocar is aligned coaxially or substantially coaxially with the elongate body. Generally, the alignment of the grasping assembly 20 or trocar 30 allows insertion of the grasping assembly and a section of the elongate body into a subject. For example, the trocar and the elongate body may each have longitudinal axes that are parallel to one another. The two longitudinal axes may be coaxial or they may be offset. If they are offset, they are preferably offset by a distance equal to or less than the width or diameter of the elongate body, and more preferably equal to or less than half the width or half the diameter of the elongate body.

In one embodiment, the elongate body has two opposing parallel sides defining the width of the elongate body. The trocar also has two opposing parallel sides defining the width of the trocar. One edge of the trocar is aligned parallel with one edge of the elongate body. This is shown in FIG. 4. Such an alignment, as well as coaxial or substantially coaxial alignment, provides a narrow profile to the forceps to allow easy insertion into a tissue.

The trocar preferably has a width or diameter that is equal to or less than the width or diameter of the elongate body.

The trocar can be any suitable shape for piercing tissues or other materials. For example, the trocar is generally pointed and can be conical. Alternatively, the trocar may comprise a sharp tip comprised of a number of planar sides, for example 3 or 4 sides forming a pyramidal shape. In some embodiments, the trocar comprises an elongate section with a tapered end or point, as shown in FIG. 4. The grasping assembly shown in FIG. 4 comprises a trocar with an elongate section integral with a conical pointed section. The trocar allows the forceps to pierce tissue and other materials. In this way, the forceps of the invention can be inserted into a patient or tissue without requiring a separate incision.

The grasper 40 can be attached to the grasping assembly 20 by way of a pin 44 which forms a pivot about which the grasper moves, as shown in FIG. 4. Alternatively, the grasper can be attached to the elongate body 10 by way of a similar pin forming a pivot, or the grasper can be attached to the grasping assembly or elongate body by another type of hinge or attachment means. Accordingly, the grasper has open and closed positions that correspond to the open and closed positions of the lever 70 and the movable grasper can be said to be a hinged grasper. Closing of the grasper comprises pivotal movement of the grasper relative to the elongate body. In some embodiments of the invention, the grasper can be curved in cross section such that the curvature of the grasper is complementary to the curvature of the trocar. This provides a sleeker profile when the grasper is in the closed position to reduce damage caused when the trocar-tipped forceps of the invention are inserted into a subject or into a tissue or other material.

In alternative embodiments, the open and closed positions of the lever 70 may correspond with the closed and open positions, respectively, of the grasper 40.

In a preferred embodiment, the movable grasper comprises a shaft 41 and one or more teeth 42 that project perpendicularly or substantially perpendicularly to the shaft 41 of the grasper 40, as shown in FIG. 4. The tooth assists in grasping the tissue or surgical instrument to which the forceps 2 is applied. The tooth or teeth may be present at one end of the shaft 41 (the end opposite to the end that is connected to the grasping assembly or trocar) or they may be present along the length of the shaft.

Figure 8:
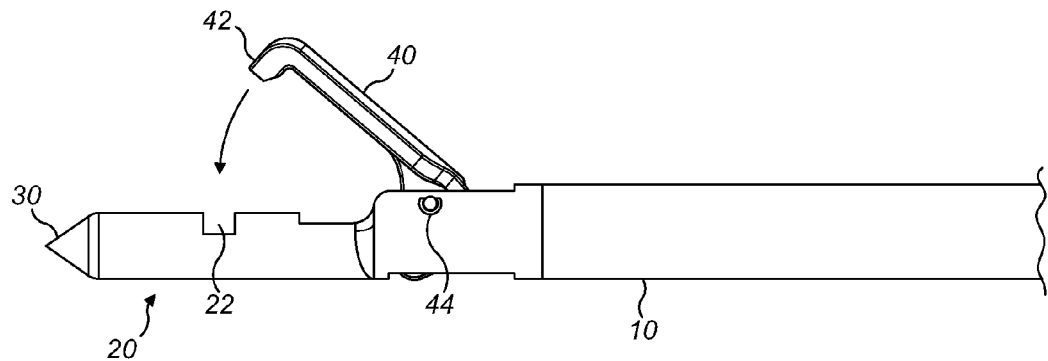
FIG. 8 is a close up side-on view of the grasping region of the adapted forceps of the invention, wherein the grasping assembly additionally has an indentation adapted to receive a tooth of the movable grasper.
Figure 9:
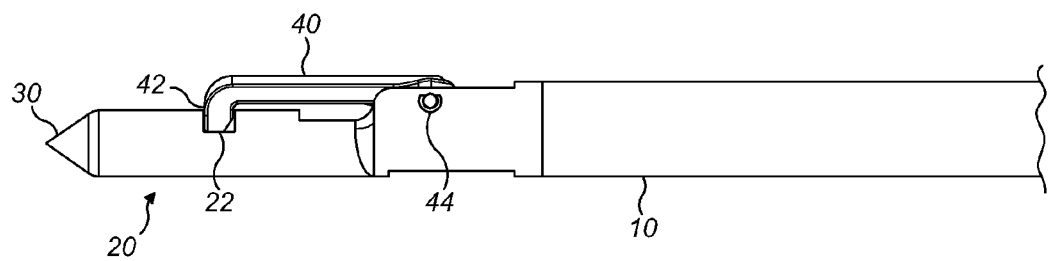
FIG. 9 is a close up side-on view of the grasping region of the adapted forceps of the invention, wherein the grasping assembly additionally comprises an indentation and the forceps is closed. The tooth of the movable grasper fits inside the indentation.

In more preferred embodiments, the grasping assembly comprises one or more indentations 22 in the trocar 30 that are adapted to receive the tooth or teeth 42 of the movable grasper 40, as shown in FIG. 8. The indentation or indentations 22 are therefore aligned with the tooth or teeth 42 such that the tooth or teeth rest within the indentation or indentations when the movable grasper 40 is in the closed position, as shown in FIG. 9. The indentation allows the teeth to be present without adversely affecting the profile of the trocar tip. This helps to ensure atraumatic entry into tissues when the forceps of the invention are inserted into a subject or tissue.

In another embodiment of the invention, the tooth or teeth may be curved such that they are complimentary to the surface of the trocar. This provides an even better fit between the grasper and trocar and provides a still narrower profile of the trocar tipped forceps. The shaft of the grasper may be curved in addition to the teeth being curved to further improve the profile of the trocar tip.

In embodiments of the invention, the actuating mechanism couples the lever to the grasping assembly for effecting synchronised pivotal movement of the lever and the movable grasper relative to the elongate body.

Figure 5:
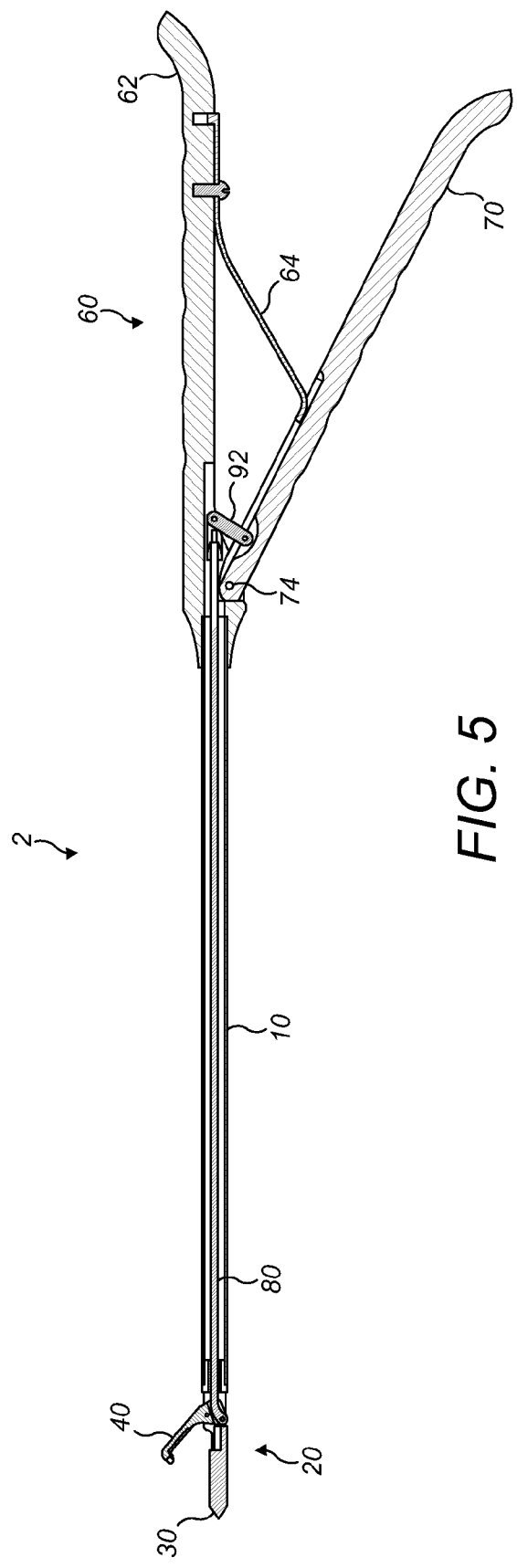
FIG. 5 is a cross-sectional view of the side of the adapted forceps of the invention showing an internal mechanism.
Figure 6:
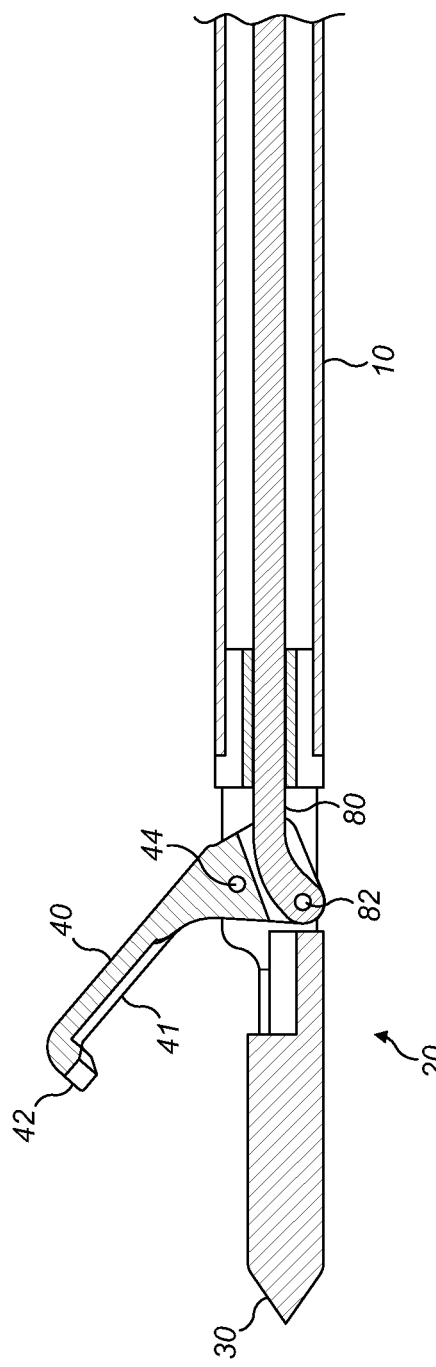
FIG. 6 is a close up cross-sectional view of the grasping region of the adapted forceps of the invention.
Figure 7:
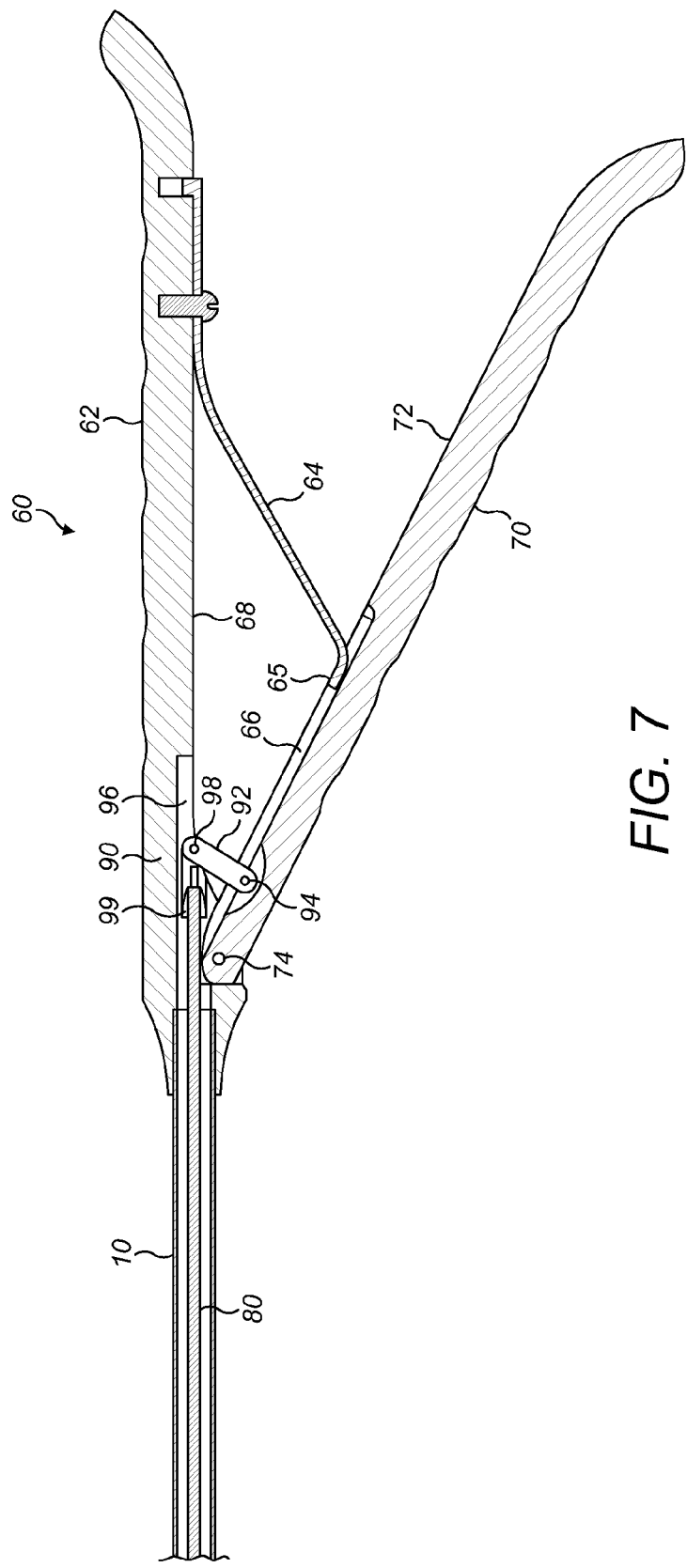
FIG. 7 is a close up cross sectional view of the intersection between the elongate body and the gripping region of the adapted forceps of the invention.

Referring to FIGS. 5 to 7, in some embodiments the actuating mechanism of the forceps 2 can be a rod 80 that is aligned parallel or substantially parallel to the elongate body 10. The actuating mechanism or rod mechanically couples the lever 70 to the grasper 40 such that when the lever is activated by a user, the grasper moves into the closed position. Closing of the grasper involves pivotal movement of the grasper relative to the elongate body. When the grasper is fully closed, the grasper is aligned substantially parallel to the elongate body. In some embodiments, the lever is also aligned substantially parallel to the handle and/or the elongate body when the grasper is fully closed.

In a preferred embodiment, the elongate body is hollow and part or whole of the actuating mechanism is contained inside the elongate body. For example, if the actuating mechanism includes a rod, this may be contained within the elongate body. This is shown in FIG. 5.

In one embodiment of the invention, the actuating mechanism may also comprise a coupling means 90 which couples closing of the lever with a retraction of the rod inside the elongate member. Retraction refers to the movement of the rod towards the grip region. Extension refers to movement of the rod towards the grasping assembly.

As shown in FIG. 7, the coupling means includes a plate 92 that is attached to the lever at one end by a pin 94. This pin allows pivotal movement of the plate relative to the lever. The opposite end of the plate 92 is attached to a folded plate 99 by a pin 98. The pin 98 permits pivotal movement of the plate 92 relative to the folded plate 99. The folded plate 99 is attached to the rod such that retraction of the folded plate 99 also causes retraction of the rod 80. In this embodiment, the coupling means comprises the plate 92, the pin 94, the pin 98 and the folded plate 99. The handle may also include a slot 96 in the planar surface 68 of the handle 62 which houses the whole or part of the coupling means 90.

In this embodiment, the elongate member 10 is hollow and as the lever is closed, the plate 92 moves about the pivots at 94 and 98. The folded plate 99 is retracted inside the slot 96 and this causes the rod 80 to be retracted relative to the elongate member 10. In some embodiments, the closing of the lever 70 causes the resilient bias 64 (if present) to contract or bend. If the resilient bias is a flexible member as shown in FIG. 7, the flange 65 is guided along the channel 66 of the lever 70. The flexible member therefore moves towards the planar surface 68 of the handle 62.

In one embodiment, at the opposite end of the forceps at the grasping assembly, as shown in FIG. 6, the rod 80 is attached to the movable grasper 40 by means of a pin 82. As the rod retracts relative to the elongate member 10, the grasper rotates about its pivot at 44 and the grasper moves into the closed position. The shaft 41 and optional teeth 42 of the grasper move towards the trocar 30 and are able to grasp tissue or other surgical devices by exerting a force in the direction of movement of the grasper.

As the pressure exerted by the user on the handle is released, the resilient bias returns the lever to the open position. The plate 92 rotates about its pivots at 94 and 98. This causes the folded plate 99 mechanism 90 to extend along the slot 96 and consequently the rod 80 extends along the elongate member 10 towards the grasping assembly 20. As the rod 80 extends towards the grasping assembly 20, the movable grasper 40 rotates about its pivot at 44 and the movable grasper 40 is returned to the open position.

The forceps can be made of any suitable materials known to a person of skill in the art. For example, the stapler may include plastics (such as polyamide, polystyrene, polyvinyl chloride, polypropylene, polyurethanes, polycarbonates or polyetheretherketone), metals (such as stainless steel or titanium) or porcelain. The forceps may be made of a mixture of these materials.

Tissues pierced by the trocar-tipped forceps are generally biological tissues such as the bowel or intestinal wall, the wall of the oesophagus, the posterior rectus sheath, a distal rectal stump or the peritoneum. Other tissues include the external tissues of the body, for example the skin, or organs generally.

In a second aspect of the invention there is provided a kit of parts comprising a forceps of the invention and a stapler apparatus.

Figure 10:
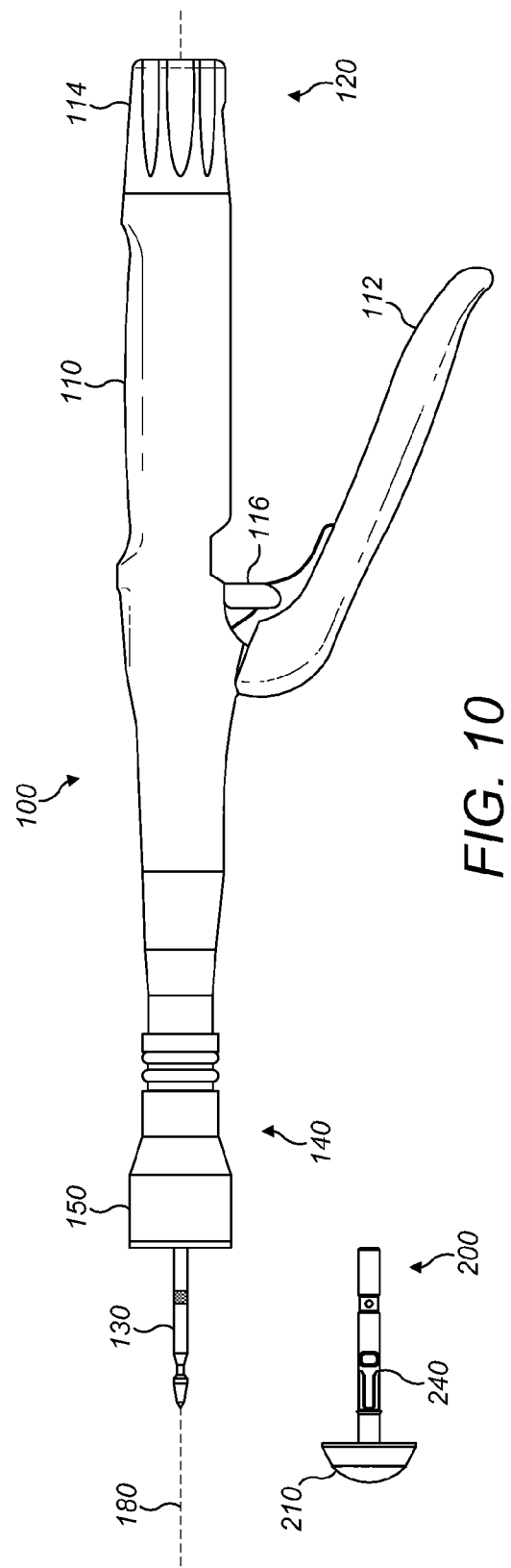
FIG. 10 shows a stapler apparatus comprising a stapler and an anvil. The forceps of the invention can be adapted to be insertable into the anvil.

The stapler apparatus as shown in FIG. 10 comprises:
(a) a stapler 100 having a proximal end 120, a distal end 140 and a longitudinal axis 180, the stapler 100 further comprising
  (i) a trigger 112;
  (ii) an anvil docking pin 130 aligned parallel (or substantially parallel) with the longitudinal axis 180 of the stapler 100; and
  (iii) a stapling means 150, the anvil docking pin 130 and stapling means 150 being at the distal end 140 of the stapler 100; and
(b) a detachable anvil 200, comprising an anvil head 220 and an anvil shaft 240,
wherein the anvil shaft 240 is adapted to receive the anvil docking pin 130 and operation of the trigger 112 causes the stapling means 150 to be actuated,
wherein the trocar of the forceps is adapted for insertion into the anvil shaft.

References to the "proximal" and "distal" ends of the stapler refer to the relative distance of the two ends of the stapler from the user when the stapler apparatus is being operated. The proximal end is that closest to the user and so usually comprises a grip area and trigger for actuation of the stapling means. The distal end is further away from the user, but is closer to the patient to whom the stapling apparatus is being applied, and so in general where the stapling means and anvil docking pin are situated.

Generally, the longitudinal axis extends between the proximal and distal ends and passes substantially through the centre of the stapler.

Figure 15:
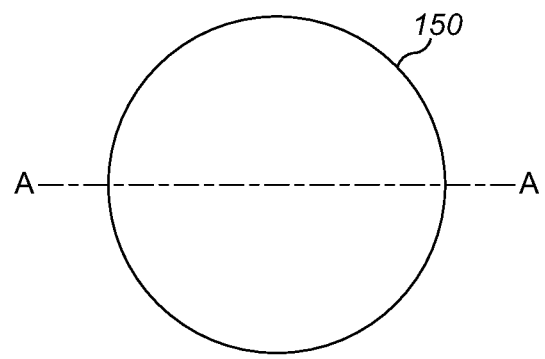
FIG. 15 shows the cross section of the stapler through the line A-A in FIG. 15.

References to "circular" include substantially circular and other configurations which would be apparent to a person of skill in the art that provides an appropriate arrangement of staples. For example, as shown in FIG. 15, the cross section of the stapling means can be circular so as to be able to provide a substantially circular configuration of staples, although an elliptical arrangement can also be used. Generally, the anvil head, the anvil shaft, the anvil docking pin and the stapling means are all substantially circular in cross section, although other arrangements may be possible provided they are able to deliver a suitable arrangement of staples.

The stapler generally has an elongate body, preferably a substantially cylindrical body. It is preferably shaped so as to allow insertion into the appropriate tissues and organs.

The body of the stapler includes trigger 112 and a stapling means 150. Preferably, the body of the stapler is substantially straight and is not bent or curved. This is useful depending on the anatomy and organs to which the stapler apparatus is being applied. In those embodiments where the body of the stapler is straight or substantially straight (as opposed to bent or curved), this also provides greater control over the stapler since there are less oscillations and movement during operation, which has an impact on the quality of the anastomosis or stoma trephine. For example, the stapler can be kept parallel to the rectal wall more easily than if the stapler was curved.

In some embodiments, the stapler comprises a grip area 110 which is intended to be held by the user when the stapler is being used. The grip area is usually positioned towards the proximal end 120 of the stapler (stapling can therefore be carried out at a distance from the user), although may be present elsewhere on the stapler.

The stapler apparatus can be used in a variety of surgical applications, for example the formation of anastomoses, stomas or stoma trephines. These can be in, for example, the gastrointestinal (GI) or between the GI tract and the exterior of the body, but more generally could be used in any tubular organs or those organs having a lumen. The stapler apparatus is therefore suitable as a surgical stapler or, in some more specific embodiments, as an intraluminal stapler. Moreover, given the substantially circular arrangements of staples delivered in some embodiments, the apparatus can be said to be a circular stapler apparatus.

Usually the stapler apparatus is disposable and will be disposed of after use. In a preferred embodiment, the stapler apparatus is sterile.

In some embodiments, the length of the anvil shaft is 4, 5, 6, 7, 8, 9 to 10 cm in length. In some embodiments, the length of the anvil shaft is at least 4, 5, 6, 7, 8, 9 to 10 cm. In some preferred embodiments, the length of the anvil shaft is in the range of 4 to 50 cm, more preferably in the ranges of 4 to 25 cm, 4 to 20 cm, 4 to 15 cm, 4 to 12 cm, 4 to 10 cm, 5 to 50 cm, 5 to 25 cm, 5 to 20 cm, 5 to 15 cm, 5 to 12 cm, 5 to 10 cm, 6 to 50 cm, 6 to 25 cm, 6 to 20 cm, 6 to 15 cm, 6 to 12 cm or 6 to 10 cm.

In some embodiments of the invention, the overall working length of the stapler has been reduced from the industry standard of 420 mm to between 250 to 400 mm, preferably between 300 and 350 mm, more preferably between 310 and 340 mm, and most preferably between 320 and 330 mm or to 325 mm. This reduced overall working length of the stapler provides a better, more stable and ergonomic platform to enhance user control of the stapler device during manipulation and firing of stapler apparatus.

In some embodiments, for example where the anvil shaft is at least 4 cm in length, the anvil of the stapler apparatus is elongated compared to the anvils of the prior art, and this elongation of the anvil shaft provides several advantages over the prior art.

For example, the presence of a longer anvil shaft means the anvil is more easily manipulated by the user and moreover it is possible to carry out the docking procedure endoanally or extracorporeally.

The elongated shaft also allows the anvil to be grasped by the surgeon endoanally or extracorporeally, or allows the surgeon to grasp it internally and bring the anvil shaft into an endo-anal or extracorporeal position. With shorter anvil shafts, docking of the anvil onto the stapler occurs inside the body of a patient, so it is difficult for a surgeon to insert the anvil docking pin into the anvil shaft and difficult to see if the anvil has fully docked over the anvil docking pin. An elongated anvil shaft allows the shaft to be brought into the endo-anal or extracorporeal position.

Consequently, the elongated anvil shaft allows the surgeon to see more clearly where the anvil is to aid docking onto the anvil docking pin. The elongated shaft also allows the surgeon to see extracorporeally that the anvil has fully engaged with the stapler. Hence the elongated shaft provides a visualisation advantage over the prior art. In staplers with shorter anvils, the anvil shaft is obscured or surrounded by tissue that makes it difficult to locate the anvil shaft or difficult to grasp the shaft in order to maneuver it into position. However, extending the anvil shaft of the stapler described herein removes his problem.

Moreover, since the anvil shaft is more easily seen by the surgeon, it is also easier for the surgeon to ensure that complete docking of the anvil shaft on the anvil docking pin is achieved. Staplers with short anvil shafts rely on an audible "click" alone to ensure docking. In contrast, the stapler described herein additionally provides visual confirmation that docking has occurred. Hence the stapler provides additional safety for the patients.

The elongated anvil shaft enables passage from internal body habitus to the endo-anal or extracorporeal space for docking to the stapler. The length of this elongation is only limited by modifications to interior drive shafts of the stapler that facilitate movement (retraction and extension) of the anvil docking pin and engaged anvil shaft into and out of the stapler.

Figure 11:
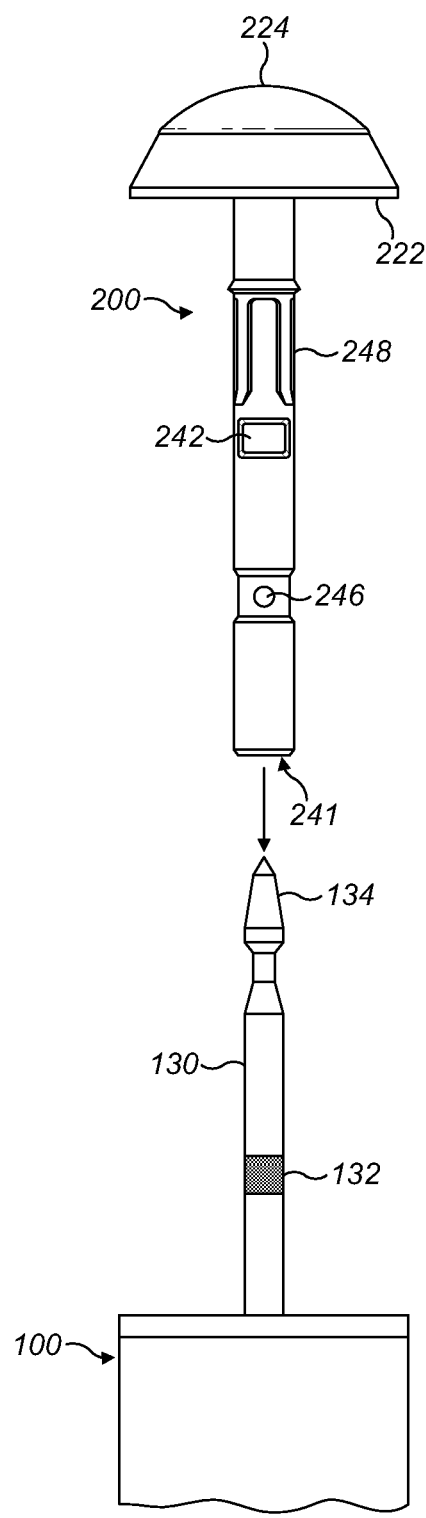
FIG. 11 shows the anvil in alignment ready for docking on to the stapler.

The anvil docking pin can be similarly altered in length to accommodate the different lengths of the anvil shaft. Usually, the anvil docking pin extends into the stapler such that only a section of the anvil docking pin is visible when the stapler is viewed from the side, as in FIG. 10. The anvil docking pin has a smaller diameter than the anvil shaft, allowing the anvil docking pin to be inserted into the anvil docking pin. In particular, the anvil docking pin has a diameter equal to or less than the internal chamber 241 of the anvil shaft 240, as shown in FIG. 11. In a preferred embodiment, the anvil docking pin is aligned coaxially or substantially coaxially (for example within a distance that is equal to the width or diameter of the anvil docking pin, or any distance that allows a suitably spaced distribution of staples around the anvil docking pin) with the longitudinal axis of the stapler.

The anvil docking pin can be blunt or it can be trocar tipped. A trocar tipped anvil docking pin, such as that shown in FIG. 10, has the advantage of being able to pierce tissues. For example, when creating an anastomosis between a section of bowel and a rectal stump in the lower rectum, the rectal stump may be closed off using sutures or staples and the trocar tipped anvil docking pin can be used to pierce the rectal stump staple line and engage with the anvil. This ensures that the stapler is suitably positioned to allow the dispensed staples to pass through both the distal stump and the colon that is attached to the anvil by way of, for example, a purse string suture.

The staples delivered by the stapling means can be arranged so as provide a substantially circular arrangement. The arrangement of staples is referred to as the staple line. The staples may be positioned such that they are aligned with the circumference of the circular staple line. Alternatively, they may be aligned with the radius of the circle staple line, or at an angle between the radius and the circumference of the circle. Multiple rows of staples may be present, for example 2, 3, 4 or 5 rows of staples. In some embodiments the stapling device will be presented with the option of either two or three or more concentric rows of staples mounted circumferentially within the staple housing.

The trigger 112 can be in the form of, for example, a lever, as shown in FIG. 10. In such embodiments, activation of the trigger causes the stapling means to be activated by way of mechanical transfer of force or energy. Alternatively, the trigger may simply be a push button which causes the stapling means to be actuated automatically, for example by the use of electrically powered internal components.

Figure 14:
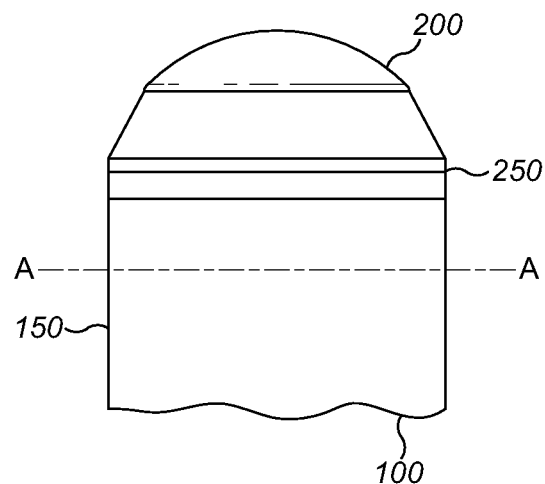
FIG. 14 shows the anvil retracted into the stapler. The tissue or tissues to be stapled would be disposed at the interface 250 of the anvil head 220 and stapling means 150.

The grip area and trigger of the stapler are preferably arranged such that when a user grasps the stapler by the grip area, the user can simultaneously activate the trigger. For example, as shown in FIG. 10, the trigger (which, in the embodiment shown in FIG. 10, is a lever) may be attached to the stapler at a central portion of the stapler and the grip area may extend towards the proximal end of the stapler In some embodiments, the distal end of the stapler also comprises a retracting means 114, as shown in FIG. 10. This retracting means can be rotated by the user and reversibly retracts the anvil docking pin (and anvil if engaged with the anvil docking pin) along the longitudinal axis of the stapler into the stapler body. If an anvil is engaged with the anvil docking pin, this causes the anvil head to move closer to the stapling means. FIG. 14 shows an anvil 200 fully engaged with a stapler 100 and fully retracted into the stapler. The components of the stapling apparatus are arranged such that the tissues to be stapled together are trapped or secured between the anvil head and the stapling means. The tissues to be stapled together are trapped at the interface 250 of the anvil 200 and stapling means 150. When the device is in use during surgery, the anvil head and stapling means will usually not come into direct contact with one another since there will be a layer or layers of tissue disposed between the two components at the interface 250 of the anvil head and stapling means.

The anvil docking pin (and anvil if engaged with the anvil docking pin) can be removed from the inside of the stapler by rotating the retracting means in the opposite direction. Alternatively, the anvil can simply be pulled off the anvil docking pin by the user.

In preferred embodiments, activation of the trigger is only performed after the retracting means has been rotated to move the anvil head closer to the stapling means and the tissues to be stapled together are trapped between the anvil head and the stapling means.

The retracting means can achieve the effect of guiding the anvil docking pin into the stapler along the longitudinal axis by any suitable means, for example a rod in the stapler body that couples the retracting means to the anvil docking pin, either directly or via intermediate components. The rod may have a screw thread that causes the anvil docking pin to be retracted into the stapler without causing the anvil docking pin to rotate. Other retraction mechanisms would be apparent to a person of skill in the art.

The retracting means may comprise flanges that extend outwards from the retracting means and/or grooves that are cut into the retracting means that allow the user to turn the retracting means more easily. The retracting means 114 as shown in FIG. 10 comprises grooves which make turning the retracting means easier for the user.

Activation of the stapler trigger causes the stapling means to be actuated. In some embodiments, the apparatus is arranged during use such that one surface to be stapled is connected to the anvil via the anvil head. The other surface to be stapled is positioned relative to the stapling means in such a way so as to allow actuation of the stapling means to connect both surfaces with staples. Preferably, the surfaces to be stapled are maintained at the interface 250 between the anvil head and the stapling means.

In some embodiments, the retracting means is absent and activation of the trigger causes both the anvil docking pin (and anvil if the anvil is engaged with the stapler) to move towards the proximal end of the stapler, and the stapling means to be actuated.

In some embodiments of the invention, the anvil head cross section in the transverse plane is substantially circular and the diameter differs according to the tissue being stapled. For example, the diameter of the anvil head may be in the range of 10 to 50 mm, more preferably in the range of 20 to 35 mm. In some embodiments, the diameter of the anvil head is 21, 25, 28 or 32 mm.

In certain embodiments, the anvil is equipped with colour markings that provide instant visual information to the user regarding the diameter of the anvil head. Generally, the diameter of the anvil head will correspond to the diameter of the stapling means such that the anvil head and the stapling means align when the anvil docking pin is retracted into the stapler. The stapler may also be equipped with corresponding colour markings that provide information to the user regarding the diameter of the stapler. The diameter of the stapling means may be in the range of 10 to 50 mm, more preferably in the range of 20 to 35 mm. In some embodiments, the diameter of the stapling means is 21, 25, 28 or 32 mm.

In one embodiment of the invention, the stapler also comprises a safety catch (116), as shown in FIG. 10. This safety catch is movable by the user and can be reversibly engaged. When the safety catch is engaged, it prevents the trigger from being activated by the user. Consequently, the safety catch can prevent the stapler from being actuated accidentally. When the safety catch is disengaged, the trigger can be fully activated and hence the stapling means can be actuated.

The stapling means comprises a stapler housing, a circular or cylindrical blade, a row of circumferentially arranged staple slots around the outside of the circular blade, and a driving blade. The circular blade and driving blade are movable substantially parallel to the longitudinal axis of the stapler. The diameter of the stapling means usually refers to the diameter of the stapler housing.

The staple slots are provided with staples when the stapler apparatus is to be used. The staples for use in the stapler apparatus generally comprise a continuous piece of metal or plastic which is deformable. The continuous piece of metal or plastic is bent so as to form a crown and two sharp or pointed legs substantially perpendicular to the crown. The legs pierce the material being stapled. The length of these legs determines the height of the staple and can be varied according to the thicknesses of the tissues being stapled. Example leg lengths (and hence staple heights) include 2, 3, 4, 4.2, 5, 6, 7, 8, 9, 10, 15, 20, 25, 30, 35, 40 and 50 mm, preferably between 2 and 30 mm or between 3 and 20 mm or between 4 and 15 mm. When the staples are installed in the stapler, the legs point towards the distal end of the stapler.

The length of the crown can also vary, for example they crown may have a length of 2, 3, 3.8, 4, 5, 6, 7, 8, 9, 10, 11, 12, 13, 14 or 15 mm. Preferably, the length of the crown is between 3 and 15 mm or between 3 and 10 mm. The length of the crown determines the distance of the legs from each other.

The staples can be made of any suitable material, for example titanium, titanium alloys (for example nitinol, also known as nickel titanium since it is an alloy of titanium and nickel) or stainless steel or other metal or plastic suitable for surgical purposes. Alternatively, biodegradable staples may be used, for example those made of mostly polylactic acid formulations.

The staples generally are initially formed into a "U" shape or similar shape prior to use, for example a rectangular or square shape wherein the staple forms three sides of the rectangle or square (for example, the legs are usually arranged substantially perpendicular to the crown).

As the trigger 112 of the stapler 100 is activated by a user, the circular blade and the staples are projected from the stapler housing. The staples are projected by the distally advancing driving blade, ejecting the staples along the longitudinal axis of the stapler and through any layers of tissue or material disposed at the interface 250 between the anvil head and the stapling means. The legs of the staples pierce the material or tissue being stapled. Once the staples have pierced the material, the legs are pressed against the anvil head so as to bend the staples inwards or outwards and hold the staples in place. The legs may be bent to the extent that they are now parallel or substantially parallel to the crown. When the legs are bent inwards, this forms a characteristic "B" shape common to many staples once used. The staples are deformed by pressing against the anvil such that they are flattened and the layers of tissue or material are held together by the flattened staples.

During actuation of the stapling means, the circular blade, or trephine, advances along the longitudinal axis to cut tissue engaged with the stapler. A ring or disc of the tissue is therefore excised by the stapler. The stapler apparatus is removed and a continuous lumen is established between the surfaces or sections of tissue being stapled together. For example, this may cause a section of bowel to become attached or reattached to another section of bowel of a rectal stump whilst maintaining a hollow lumen through which faecal matter can pass. Alternatively, the circular blade may establish a stoma between an internal lumen (such as that inside the perineal cavity or GI tract) and the exterior of the body. The circular blade has a diameter that is smaller than the diameter of the driving blade and the arrangement of the staple slots such that only a section of tissue inside the staple line is excised. The staple line is left intact to hold the two surfaces together.

Stapling means that are suitable for use in the stapler apparatus are further described in U.S. Pat. No. 4,576,167 and U.S. Pat. No. 5,758,814, the contents of which are hereby incorporated by reference.

Figure 13:
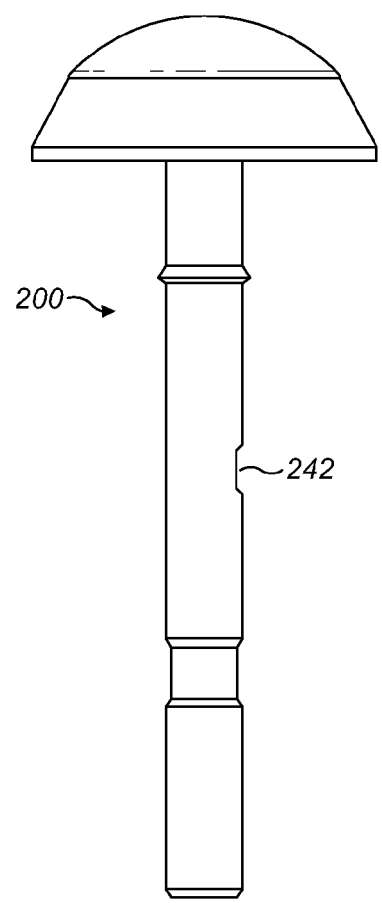
FIG. 13 shows the anvil as shown in FIG. 11, but the anvil has been rotated 90°.

In one embodiment, the anvil shaft can comprise one or more circumferential indentations 242 as show in FIGS. 11 and 13. These allow the anvil to be grasped more easily during surgery and provide greater dexterity and continuity of movement between the user and the anvil. Hence these indentations serve as gripping aids. The anvil shaft may comprise one or several indentations, example 2, 3, 4, 5, 6, 7, 8, 9, 10 or more indentations that provide this advantage. For example the anvil shaft may comprise 1 to 2, 1 to 3, 1 to 4, 1 to 5, 1 to 6, 1 to 7, 1 to 8, 1 to 9 or 1 to 10 indentations. The indentations can extend completely around the circumference of the anvil shaft, for example to form annular grooves, or they may be restricted to one section of the circumference of the anvil shaft as shown in FIGS. 11 and 13. The indentations may be present in pairs such that they do not extend around the entire circumference of the anvil shaft but are aligned so that indentations are present on opposing sides of the anvil shaft. An anvil shaft may include 1, 2, 3, 4, 5, 6, 7, 8, 9 or 10 pairs or 1 to 2, 1 to 3, 1 to 4 or 1 to 5 pairs of opposing indentations.

Figure 12:
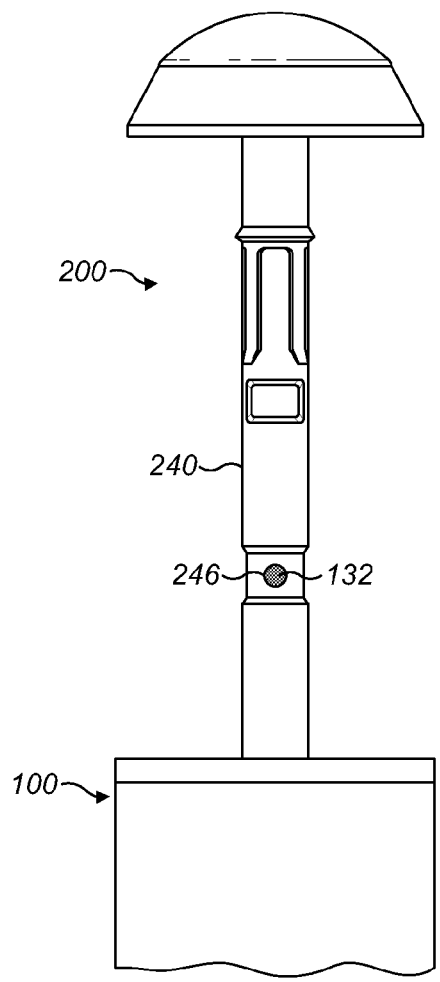
FIG. 12 shows the anvil fully docked onto the stapler.

In a further embodiment, as shown in FIG. 11 the anvil shaft 240 can comprise a viewing window 246. The anvil docking pin 130 can also comprise a docking indicator 132 such that when the anvil 200 is fully docked over the anvil docking pin 130, the docking indicator 132 is visible through the viewing window 246. FIG. 12 shows the anvil fully engaged with the anvil docking pin and the docking indicator 132 is visible through the viewing window 246.

This viewing window provides information to the user as to the extent to which the anvil is engaged with the stapler. The viewing window and docking indicator are positioned such that when the anvil is fully engaged with the stapler, only then is the docking indicator visible to the user through the viewing window. The combination of a viewing window, a docking indicator and the elongated anvil shaft provides an advantage over the prior art since endo-anal and extracorporeal docking is facilitated by the presence of an elongated shaft, and hence the viewing window and docking indicator are visible to the surgeon or other user when the stapler apparatus is being used.

The docking indicator can be a marking such that it is visually distinguishable from the rest of the anvil docking pin. For example, the docking indicator may be a section of the anvil docking pin that is coloured (for example red) to allow a quick visual confirmation that the anvil is fully engaged with the stapler. The docking indicator may extend around the entire circumference of the anvil docking pin such that the docking indicator is visible through the viewing window regardless of the relative rotational orientations of the anvil and anvil docking pin. The docking indicator is positioned on the anvil docking pin such that the docking indicator aligns with the viewing window only when the anvil is fully docked onto the anvil docking pin.

The anvil shaft 240 may include one viewing window (as shown in FIGS. 11 and 13; in FIG. 13, the anvil has been rotated 90° and hence the viewing window is no longer visible). Alternatively, the anvil shaft may include a plurality of viewing windows, for example 2, 3, 4, 5, 6, 7, 8, 9 or 10 or more, which allow the docking indicator to be seen when the anvil shaft is fully engaged with the anvil docking pin. The anvil shaft may therefore include 1 to 2, 1 to 3, 1 to 4, 1 to 5, 1 to 6, 1 to 7, 1 to 8, 1 to 9 or 1 to 10 viewing windows. Alternatively still, the anvil shaft may include a section made of a transparent or semi-transparent material that allows the docking indicator to be seen when the anvil shaft is fully engaged with the anvil docking pin. References to "viewing window" therefore include such transparent or semi-transparent sections of the anvil shaft as well as actual holes or apertures in the side of the anvil shaft.

Figure 25:
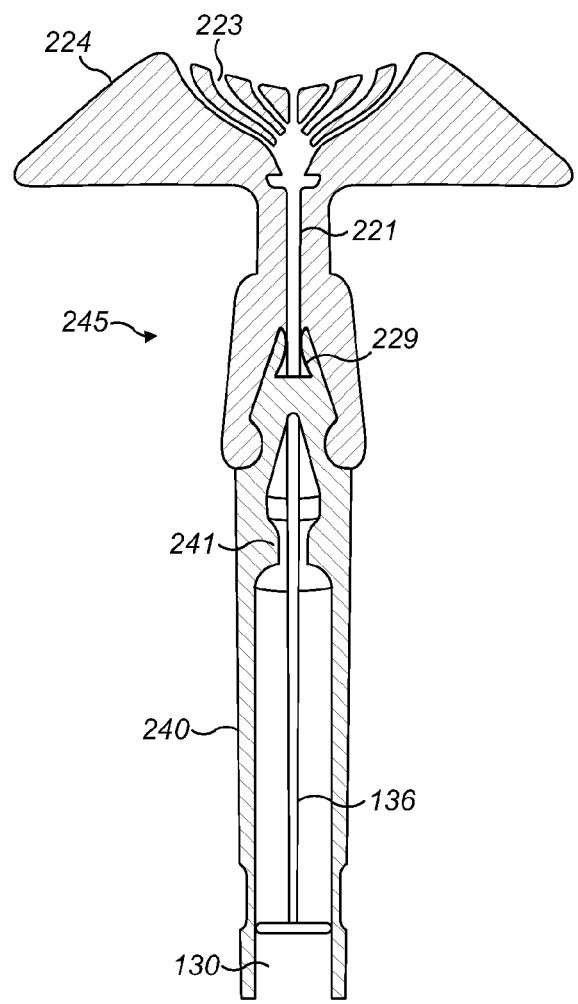
FIG. 25 shows an anvil 245 comprising a network of channels 221 docked onto an anvil docking pin 130 of a surgical stapler.

In one embodiment, since the anvil docking pin is insertable into the anvil shaft, the anvil docking pin further comprises a retaining means 134 that reversibly secures the anvil in position when the anvil is fully docked on the anvil docking pin. The anvil shaft therefore comprises an internal chamber 241 which is adapted to receive an anvil docking pin. FIG. 11 shows an anvil 200 aligned ready for docking onto the anvil docking pin 130. FIG. 25 is a cross-sectional view showing the anvil docking pin 130 inserted into the internal chamber 241 of an anvil shaft 240.

This retaining means may take the form of a narrowing and widening of the anvil docking pin in conjunction with a narrowing of the internal chamber the anvil shaft. The internal chamber of the anvil shaft is adapted to complement the shape of the anvil docking pin such that when the anvil is fully engaged with the anvil docking pin, the narrowing of the internal chamber of the anvil shaft is aligned with the narrowing of anvil docking pin, thereby causing the anvil to be removably secured in place.

As shown in FIG. 11, the retaining means may comprise an outer retaining means 248 present on the anvil shaft and an inner retaining means 134 present on the anvil docking pin. The outer retaining means can be a section of the anvil shaft that can reversibly extend beyond the circumference of the anvil shaft when a force externalizing radially from the centre of the anvil shaft is applied to the outer retaining means. The outer retaining means also corresponds to a narrowing of the inner chamber of the anvil shaft. For example, when the inner retaining means 134 comprises a narrowing and a widening of the anvil docking pin (as shown in FIG. 11) and the anvil docking pin is docked into the anvil shaft, the narrowing of the internal chamber 241 of the anvil shaft 240 causes the outer retaining means 248 of the anvil shaft 240 to be pushed outwards. When the inner retaining means 134 is pushed past the narrowing of the inner chamber 241 of the anvil shaft 240 present at the outer retaining means 248, the outer retaining means 248 returns to its original position in line with the sides of the anvil shaft 240. The narrowing of the inner chamber 241 of the anvil shaft 240 at the outer retaining means 248 corresponds to the narrowing of the diameter of the anvil docking pin 130 at the inner retaining means 134, thereby causing the anvil to be removably secured in place.

Such retaining means are sometimes referred to as a spring click docking mechanisms. Other retaining means would be apparent to a person of skill in the art. In addition to reversibly securing the anvil in place, the presence of a retaining means also has the added advantage that an audible sound is emitted as the anvil is engaged with the stapler, providing auditory confirmation to the user that the anvil is fully engaged with the stapler.

The retaining means also allows the stapler apparatus to be manipulated without the anvil becoming detached from the stapler. Hence the retaining means increases the safety of the stapler.

Preferably, the anvil head has a circular cross section in the transverse plane. The anvil head comprises two opposing surfaces 222 and 224. The anvil shaft extends outwards from the centre of one of these surfaces and is perpendicular or substantially perpendicular to the plane of the surface from which the docking pin extends. The anvil shaft is therefore connected to or integral with the anvil head at one end. In some embodiments, the anvil head comprises a flat planar surface from which the anvil shaft extends. The opposing surface may be curved, conical or frustoconical in shape. Generally the anvil head is shaped to provide an atraumatic top to the anvil when it is manipulated, either via an enterotomy (a surgical incision into the intestine) or via the natural passageways in hollow organs such as stomach, bowel, oesophagus or other hollow organs.

Alternatively, one of the opposing surfaces 222 or 224 may be concave and the other convex, the two opposing surfaces being complementary to each other and the anvil head having a thickness determined by the distance between the two opposing surfaces. In this embodiment, the anvil shaft extends from the centre of the concave surface 222. Generally, at least part of the concave surface is flat and is aligned perpendicular to the longitudinal axis of the stapler when the anvil shaft is engaged with the anvil docking pin.

The surface of the anvil head 222 from which the anvil shaft extends generally includes a series of indentations or pockets that align with the staples slots of the stapling means 150 when the anvil is engaged with the anvil docking pin and the anvil docking pin is retracted into the stapler. These indentations cause the staples to bend inwards or outwards as the stapling means is actuated. Consequently, once the staple legs pass through the tissues being stapled and are bent inwards or outwards by the anvil, the staples are secured in place and the two tissues are fixed together (such as two hollow organs when creating an anastomosis or in the creation of a stapled stoma trephine during stoma creation). The indentations in the surface of the anvil head 222 can be formed by, for example, mechanical pressing or engraving.

In one embodiment of the invention, in addition to the internal chamber 241 that is adapted to receive the anvil docking pin, the anvil shaft includes a central hollow channel 221, as shown in FIG. 25. This central hollow channel may extend from the internal chamber 241 of the anvil shaft 240 through the entire thickness of the anvil head 220 and terminate in an aperture 223 in the surface 224 of the anvil head 220. The anvil shaft may include a plurality of these channels, each terminating in separate apertures in the surface 224 of the anvil head. Alternatively, the anvil 245 may comprise one hollow channel 221 in the anvil shaft that branches out into a plurality or network of channels in the anvil head, each ending in an aperture in the surface 224 of the anvil head. FIG. 25 shows an anvil 245 according to this embodiment of the invention, wherein the anvil comprises a central hollow channel 221 branching out into a plurality of channels each ending in an aperture 223 in the surface 224 of the anvil head 220.

These channels allow air to be drawn through the anvil head when the anvil 245 is attached to a suction device 225. When suction is applied through the anvil, the anvil can be used to manipulate biological tissue or other substances by causing the tissue to become reversibly attached to the anvil head by the use of suction through the channels. The suction causes a vacuum that facilitates reversible attachment of tissue to the anvil head. The suction can be removed when the tissue is in an appropriate place or is accessible using, for example, forceps or other surgical device or a surgeon's fingers.

The suction device can have a fitting 227 that is adapted to allow the fitting to engage with the anvil shaft in the same manner as an anvil docking pin. The anvil 245 may include a seal 229 which provides an air-tight seal between the suction device and the anvil channels. The seal may be positioned where the plurality of channels inside the anvil head converge into one channel, or may be positioned further down the anvil shaft to where the fitting of the suction device terminates when the suction device is engaged with the anvil.

Figure 26:
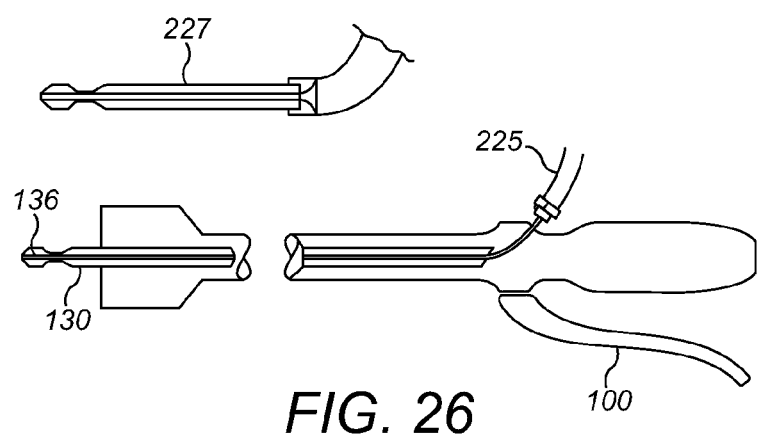
FIG. 26 shows a suction device fitting 227 and a surgical stapler 100 attached to a suction device 225.

Optionally, the anvil docking pin 130 can also be equipped with one or more hollow channels 136, as shown in FIG. 25. The hollow channels allow air to be sucked through the anvil docking pin and then through a channel (or channels) 221 and aperture (or apertures) 223 in the anvil head 220. Consequently, when the anvil is engaged with the anvil docking pin, the stapler can be attached to the suction device and tissue can be manipulated even when the anvil is engaged with the stapler. This is shown in FIG. 26. A stapler 100 is attached to a suction device 225 which draws air through the anvil docking pin 130 by means of a central channel 136 in the anvil docking pin 130.

Figure 27:
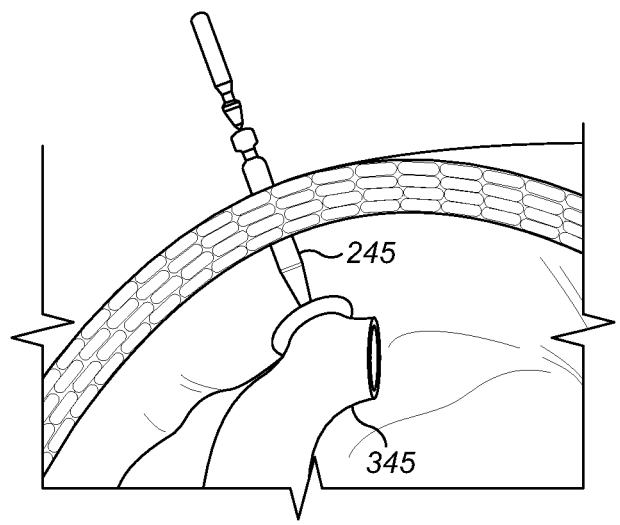
FIG. 27 shows a section of bowel 345 being manipulated by an anvil 245 when attached to a suction device.

Preferably, in these embodiments including one or more channels in the anvil head, the suction device is controllable so the amount of suction applied to the tissue can be varied and hence damage to the tissue can be prevented (atraumatic manipulation of the tissue). Manipulation of the tissue includes movement and removal of tissues and organs within the human body during a variety of surgical procedures, for example atraumatic fixation and retraction of bowel in the creation of stapled stomas, particularly to ensure the correct orientation of the bowel as it is exteriorized to form the stoma. Manipulation of a section of bowel is shown in FIG. 27.

In one embodiment the stapler apparatus further comprises a gauge on the body of the stapler that provides information to the user as to how far the anvil docking pin has been retracted into the stapler. As the user turns the retracting means, the gauge moves up and down according to how far inside the stapler the anvil docking pin has been refracted. This gauge may include certain upper and lower limits. Below the lower limit, the anvil docking pin has not been retracted sufficiently enough to allow the staples to be bent by the indentations in the anvil head to secure them in place. Above the upper limit, the anvil docking pin has been retracted so far that damage could be caused to the two tissues disposed at the interface between the anvil head and the stapling means.

In preferred embodiments, the gauge is present on the distal end of the stapler such that when the stapler is grasped by the user, the user's hand does not obscure the gauge from view.

The stapler and stapler body can be made of any suitable materials known to a person of skill in the art. For example, the stapler may include plastics (such as polyamide, polystyrene, polyvinyl chloride, polypropylene, polyurethanes, polycarbonates or polyetheretherketone), metals (such as stainless steel or titanium) or porcelain. The anvil may also be made of any of these materials.

The trocar of the forceps 2 is adapted to be insertable into the anvil shaft 240 of the stapler apparatus. The grasping assembly is preferably adapted to grasp the anvil shaft without resulting in an increase (or significant increase) in the width of the grasping assembly when engaged with an anvil shaft. The movable grasper may be arranged such that the movable grasper lies parallel to the elongate body when the grasping assembly is engaged with an anvil shaft.

The combination of the forceps 2 with a stapler apparatus is useful as the trocar 30 of the forceps 2 is adapted for insertion into the anvil shaft 240. For example, the lever 70 and/or grasper 40 of the forceps 2 are maintained in the open position when inserting the trocar 30 into the anvil shaft 240. The lever is then activated to move the lever and the grasper 40 into the closed positions. The grasper 40 then grasps the anvil 200 by the anvil shaft 240 and the anvil can thereby be securely moved using the forceps 2. Reversible attachment of the forceps 2 of the invention with a stapler anvil is shown in FIGS. 19, 20, 29*a* and 29*b*.

If a tooth 42 is present on the grasper 40, this assists in grasping the anvil 200. In particular, the tooth 42 of the grasper 40 and indentations 242 of the anvil shaft 240 may be aligned such that the tooth 42 rests in the indentation 242 of the anvil shaft 240. This allows a more secure grasping of the anvil using the forceps of the invention. Moreover, the width the grasping assembly is not increased or significantly increased after the anvil is grasped. It can be seen in FIGS. 20 and 29*a* that the tooth 42 aligns with the indentation on the anvil shaft 240 and a narrow profile is maintained.

The presence of the trocar tip 30 on the forceps 2 allows a surgeon to pierce tissues. Consequently, the forceps 2 can be used to retrieve an anvil contained inside the body or organ of a patient without requiring additional incisions. Therefore, the forceps 2 are suitable for use in laparoscopic procedures The combination of the forceps 2 and an elongated anvil shaft is particularly useful since it allows the shaft to be exteriorized in procedures where this is advantageous, for example when creating an ultra low resection and anastomosis from within 1 to 10 cm from the anal verge. The exteriorization of the anvil shaft allows the surgeon to be sure that the anvil is fully docked onto the anvil docking pin.

In some embodiments, the kits of the invention further comprise mesh reinforcement or reinforcement material. When the stapler apparatus is in use, the mesh may be placed between two layers of tissue that are being stapled together. Alternatively, the mesh may be applied above or below the tissues being stapled. This mesh or other material serves to reinforce the anastomosis or stoma trephine being formed since the applied staples pass through both layers of tissue and the mesh. The mesh may also improve the seal between the two layers of tissue to help prevent leakage of any material from the lumen of the organ into the body cavity. Mesh may also assist in preventing adverse consequences of surgery, for example parastomal herniation.

The mesh can be made of any suitable material, such as a synthetic or a biological material. When operating the device may be placed on the anvil docking pin or the anvil shaft prior to actuation of the stapling means.

Generally the mesh is wider than the width of the anvil head and stapling means. This ensures the staples engage the mesh. The mesh can be any suitable configuration, for example circular, square, ovoid and so on. If the mesh is circular, then the mesh generally has a greater diameter than the anvil and/or the stapling means. Generally, the mesh is suitably sized to overlay the entire perimeter of the anastomosis or stoma trephine.

Synthetic materials suitable for the mesh include polypropylene, polyester and polytetrafluoroethylene (PTFE, for example compressed, expanded or electro spun). Polypropylene is stable, strong, inert and has good handling qualities. The polypropylene meshes are made up of polypropylene fibres arranged in a network with pores of different sizes. PTFE meshes are smooth, soft and strong and allow good tissue ingrowths.

Biological meshes include those harvested from cows, pigs and horses such as pericardium, but also other organs including dermis tissue.

In some embodiments of the invention, the kit can further comprise a safety guard. The safety guard is made of plastic or metal or other suitable material and is intended to be positioned between the stapling means and the anvil docking pin with an engaged anvil during transportation. This protects the stapler apparatus from damage by preventing the stapling means from pressing against the anvil head. The safety guard can also prevent the stapler means from firing accidently, for example in those embodiments where the stapling means can only be actuated when the anvil docking pin is retracted far enough into the stapler.

The safety guard may be cylindrical, preferably, the safety guard comprises a central hole and is attachable onto the anvil docking pin such that the anvil docking pin passes through the central hole of the safety guard. The safety guard may also include a passage from the outer edge of the safety guard to the central hole of the safety guard that allows the safety guard to be place on or removed from the anvil docking pin even when the anvil is engaged.

In a further embodiment of the invention, the kit may further comprise tongs 370, comprising two elongate members attached to each other at one end by a flexible join (for example a hinge or pivot), the elongate members being curved at the other end. The curved section of the elongate members may be orientated at between 45° and 135° relative to the non-curved section of the elongate members (for example 90°). The elongate members are usually symmetrical in shape to one another. The curved ends of the elongate members comprise one or more curved recesses, wherein recesses in opposing elongate members are aligned with one another. This alignment may result in apertures in the tongs when the tongs are closed by a user, each aperture being defined by the aligned recesses in opposing elongate members. The recesses are adapted to receive the anvil shaft of a stapler apparatus and reversibly secure the anvil when the tongs are closed. Preferably the tongs are used to grasp the anvil shaft by the indentation or indentations 242 present in one anvil shafts of the invention. More preferably, the curvature of the curved section of the elongate members allows grasping of the anvil parallel to the longitudinal axis of the stapler. The curvature of the elongate members is between 90° and 10°, more preferably between 30° and 60° relative to the straight sections of the elongate members.

The adapted tongs provide greater dexterity to the surgeon when manipulating the anvil during a surgical procedure. The tongs may be used in such steps as the engaging and positioning steps outlined above. FIGS. 25 and 26 show the tongs 370 manipulating an anvil.

In some embodiments of the invention, the kit of parts further comprises instructions for use. In some embodiments, the kits are sterile. The kits can also be disposable.

In a third aspect of the invention there is provided a method of forming an anastomosis between two surfaces using the kit of parts of the invention comprising:

attaching a first surface to be stapled to the anvil 200 of the stapler apparatus;

piercing a second surface to be stapled with the forceps 2;

grasping the anvil 200 with the forceps 2;

engaging the anvil docking pin 130 with the anvil shaft 240;

positioning the stapler 100 to engage the stapling means 150 with a second surface to be stapled; and activating the trigger 112 to connect together the first and second surfaces with staples.

In one embodiment of the invention, the method of forming an anastomosis further comprises the step of retrieving the anvil shaft through the staple line of the second surface. The method may also comprise operating a retracting means to retract the anvil docking pin into the stapler after docking of the anvil to the anvil docking pin. The anvil may be attached to the first surface (for example a section of bowel or intestine) by way of a purse string suture or by any suitable means know to a person of skill in the art.

In such embodiments where a purse string suture is used, the first tissue is closed around the anvil shaft with a purse string suture and the anvil head is therefore enclosed in the lumen of the first tissue. The anvil shaft passes through the purse string suture and is exposed ready for docking onto the anvil docking pin. Materials used for creating the sutures include polydioxanone (PDS), polyglycolic acid, polylactic acid, nylon and polypropylene.

The step of piercing the second surface usually comprises puncturing the second surface at the centre of the circular staple line (or other suitably shaped staple line, depending on the arrangement of staples being used). The staple line refers to the desired position of the staples after actuation of the stapling means.

In order for the second surface to be stapled, the method may further comprises a step of closing a hole in the second surface using sutures or staples and the piercing the second surface with the forceps. For example, when creating an anastomosis between a section of bowel and a distal rectal stump, the distal rectal stump may be closed off or resected using sutures or staples prior to being punctured by the forceps. Alternatively, an incision may be made in the second surface allowing the anvil to be grasped using the forceps and retrieved through the incision. Since the incision or puncture is smaller than the diameter of the anvil head, this ensures correct positioning of the two surfaces (the piece of intestine and the distal rectal stump) at the interface between the anvil head and the stapling means) to allow the staples to pass through both surfaces when the stapling means is actuated.

The anvil shaft can be manipulated using the forceps. The forceps are used to retrieve the anvil shaft past the staple line in the second surface such that the first surface is guided towards the staple line of the second surface.

Once the anvil shaft has been retrieved through the staple line of the second surface, the anvil can be docked onto the stapler. The retracting means is optionally operated (as required) and the trigger is activated. The stapling means is therefore actuated and the two surfaces are fixed together with staples. The circular blade of the stapling means also ensures a continuous lumen between the lumen of the first and second surfaces or tissues and can be an end-to-end anastomosis. The lumen may be the gut lumen, depending on the location of the anastomosis.

Mesh reinforcement may be provided on the anvil shaft or anvil docking pin such that the mesh is also stapled to the anastomosis. The mesh may be positioned between the two surfaces or tissues being stapled. Alternatively, the mesh may be present above or below the surface being stapled. In some embodiments, one or more meshes may be used, for example 2, 3, 4 or 5 or more may be used.

If a mesh or meshes are used, the circular blade of the stapler apparatus will cut the mesh to ensure a continuous lumen between the two surfaces. Suturing of the outer rim of the mesh or meshes may be required to fully secure the meshes in position.

The step of positioning the stapler may include engaging the first and second surface with the interface 250 between the anvil head and the stapling means. The first and second surfaces are trapped or disposed between the surface 222 of the anvil head and the stapling means 150 such that when the stapling means is actuated by activation of the trigger 112, the legs of the staples pierces the surfaces and hold them together with staples. Advancement of the circular blade along the longitudinal axis causes a continuous lumen to be established between the two surfaces or tissues.

The surgical stapler apparatus is depicted in use for creating an anastomosis in a bowel close to the anal verge in FIGS. 28 to 31.

Figure 28:
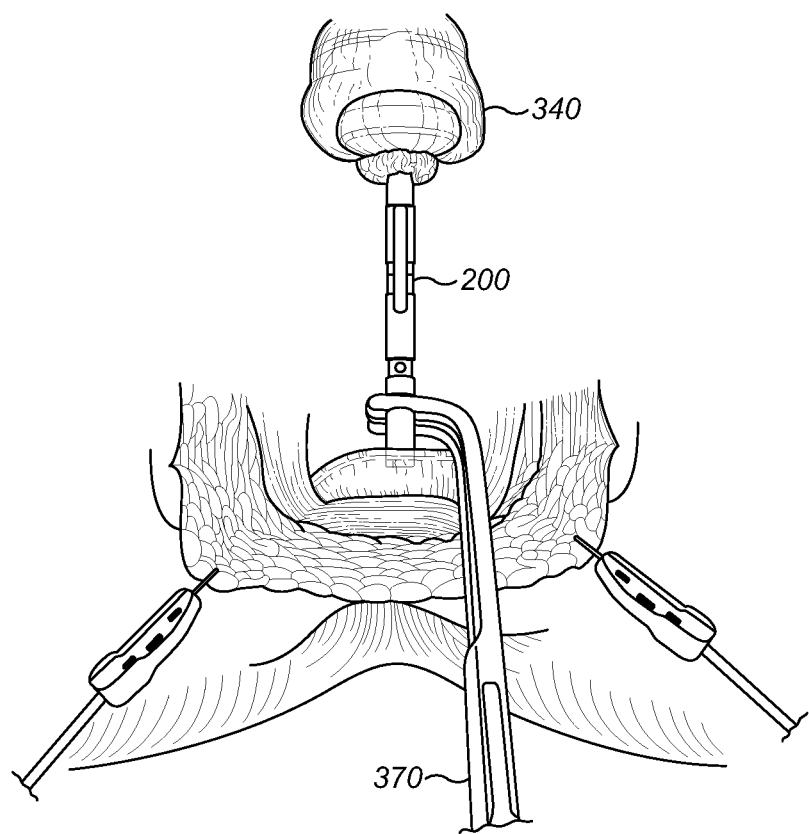
FIG. 28 shows the anvil of a stapler apparatus 200 attached to a section of intestine 340 by a purse string suture in position immediately prior to docking procedure. The anvil is manipulated using tongs 370.

FIG. 28 shows the extended anvil of the stapler in position immediately prior to the docking procedure. The anvil has been placed via purse string attachment within the proximal bowel which has been drawn into the perineal cavity by the use of specially modified anvil tongs 370 whose angle of attachment has been tailored to allow grasping of the anvil shaft parallel longitudinal axis of the stapler. The anvil shaft is grasped in at one of the indentations 242 positioned along the anvil shaft. Alternatively, standard forceps can be used. The anvil shaft is positioned above the remaining distal rectal stump 350 that was previously resected with a linear stapling device or sutures.

Figure 29A:
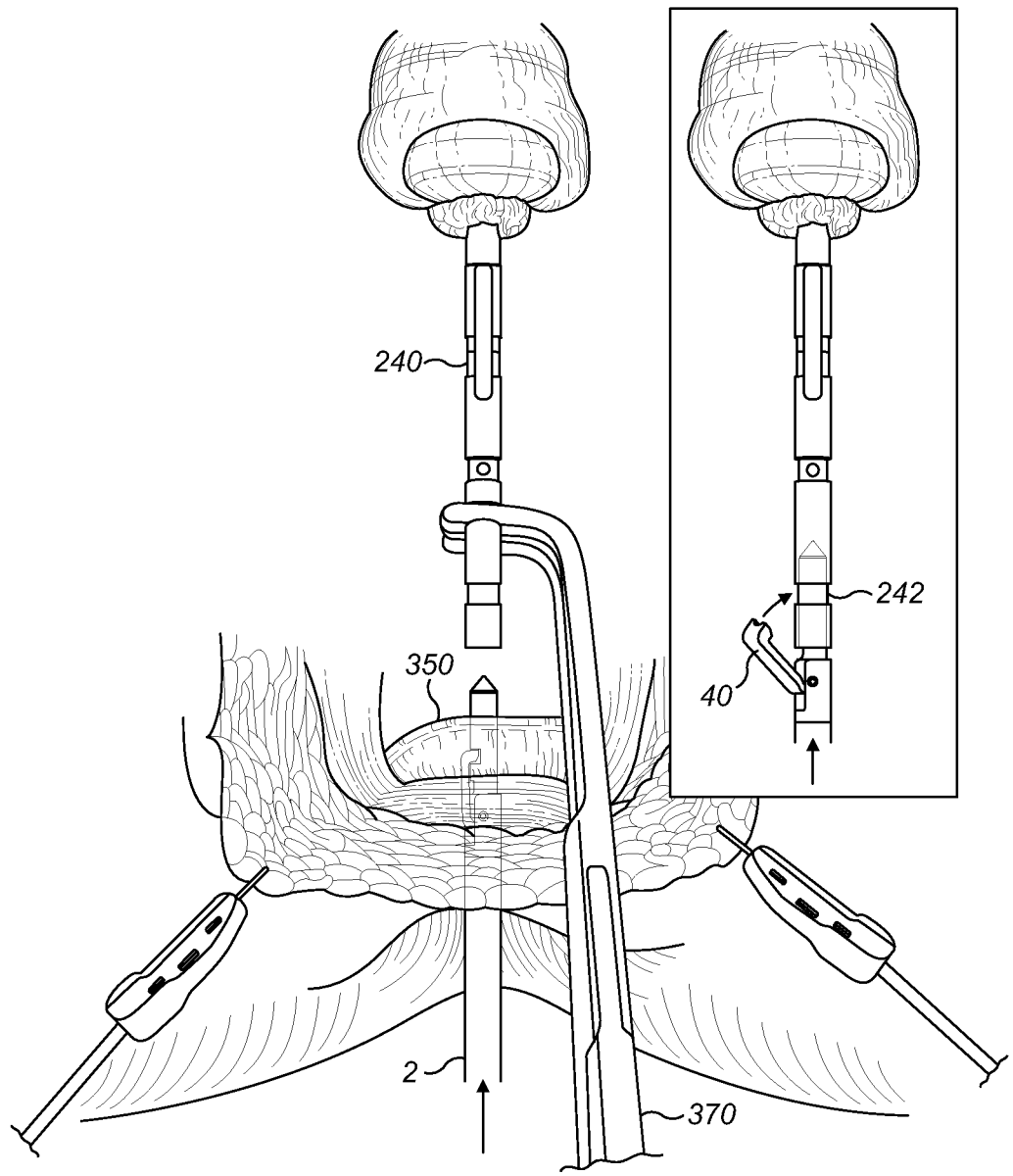
FIGS. 29a and 29b show the forceps 2 of the invention being used to secure, retrieve and draw the anvil shaft 240 through an enterotomy created in the distal rectal stump 350 after puncturing with the forceps 2. The grasper 40 grasps the anvil shaft with a tooth 42 aligning with an indentation 242.
Figure 29B:
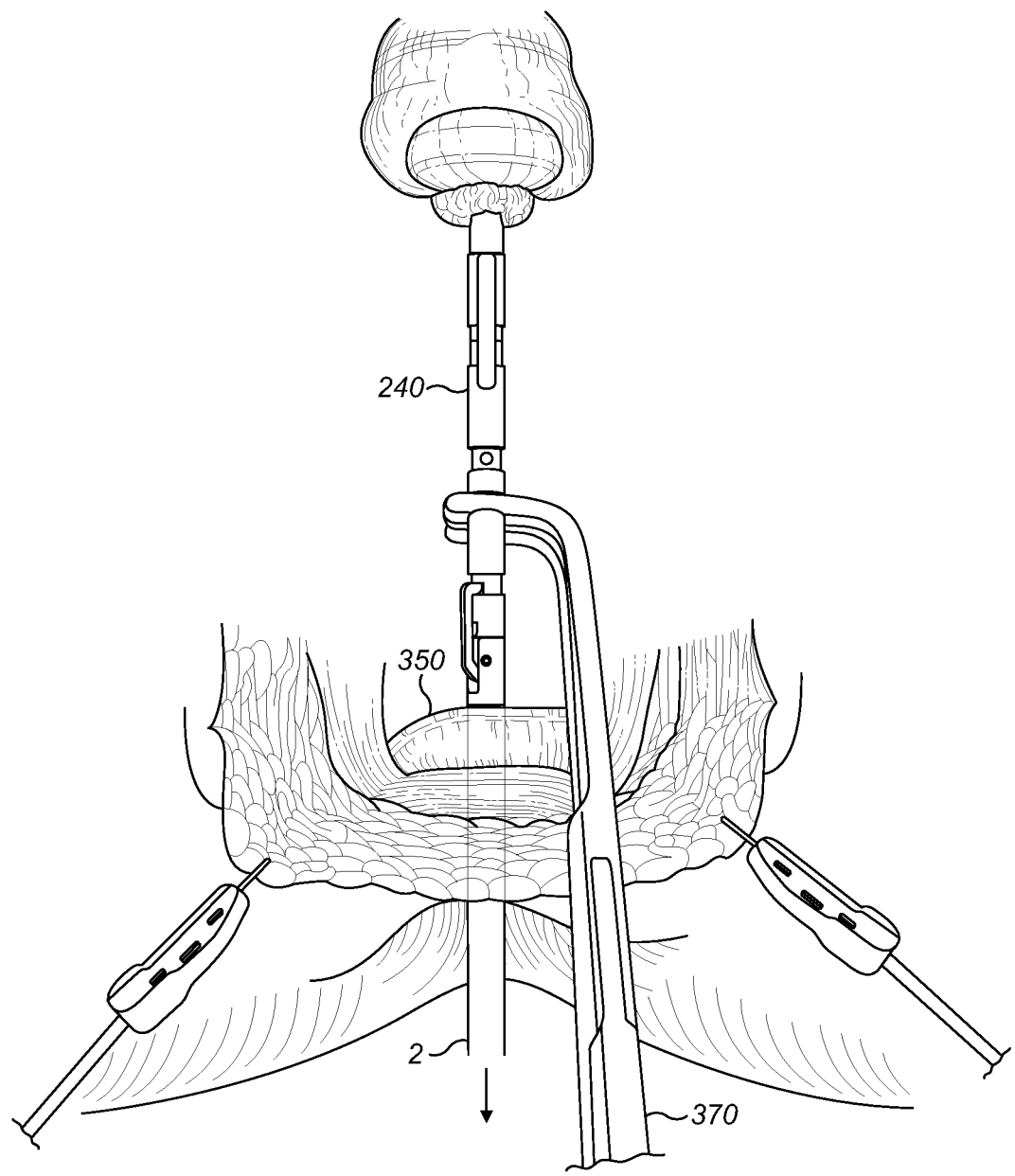

FIGS. 29a and 29b shows the forceps of the invention traversing the distal stump staple line and grasping the anvil of the stapler apparatus to secure, retrieve and draw the anvil shaft through the enterotomy created in the distal stump. The forceps 2 of the invention allow piercing of the distal stump staple line without causing excessive damage to the tissue. In addition, the profile of the forceps allows the anvil to be externalised though the distal stump staple line without causing further damage to the tissue. The tooth of the movable grasper is located to align with the indentations on the anvil shaft to provide a more secure connection between the forceps and the anvil and also to maintain a narrow profile of the trocar tip of the forceps, even when engaged with an anvil shaft.

Figure 30A:
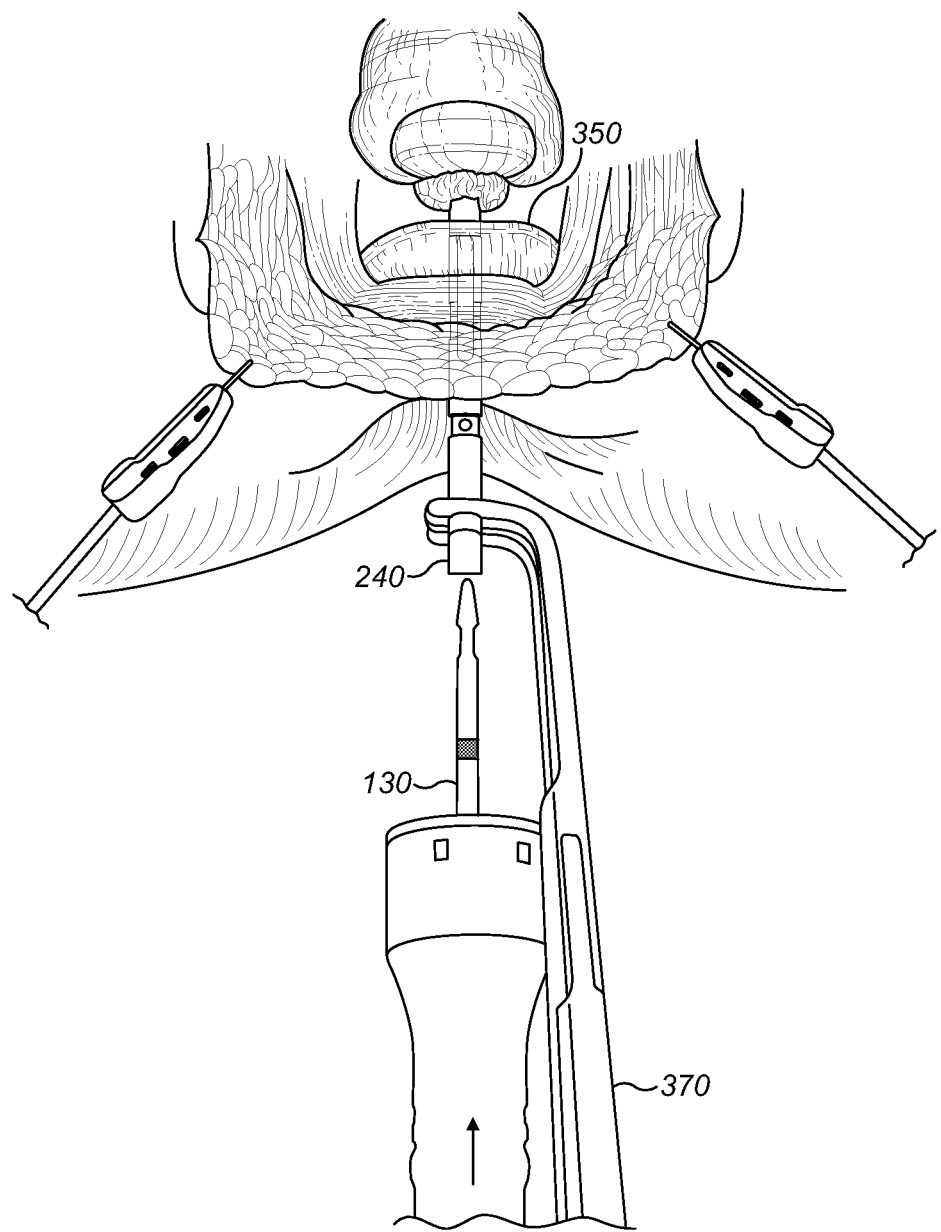
FIGS. 30a and 30b show the anvil shaft 240 fully retrieved through the distal stump 350 and fully externalised in preparation for endo-anal or extracorporeal docking of the anvil shaft 240 and anvil docking pin 130. The anvil is steadied using tongs 370.
Figure 30B:
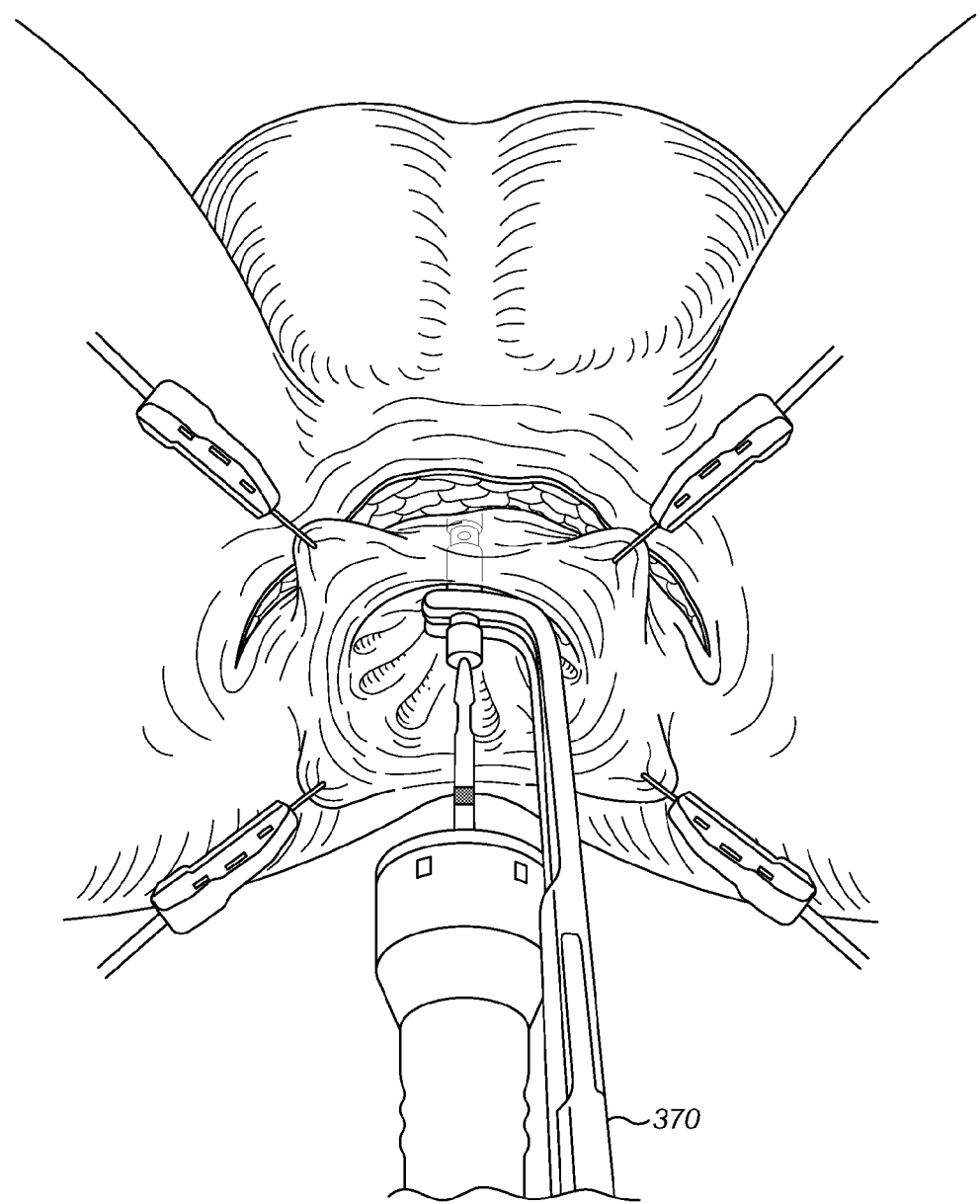
Figure 31A:
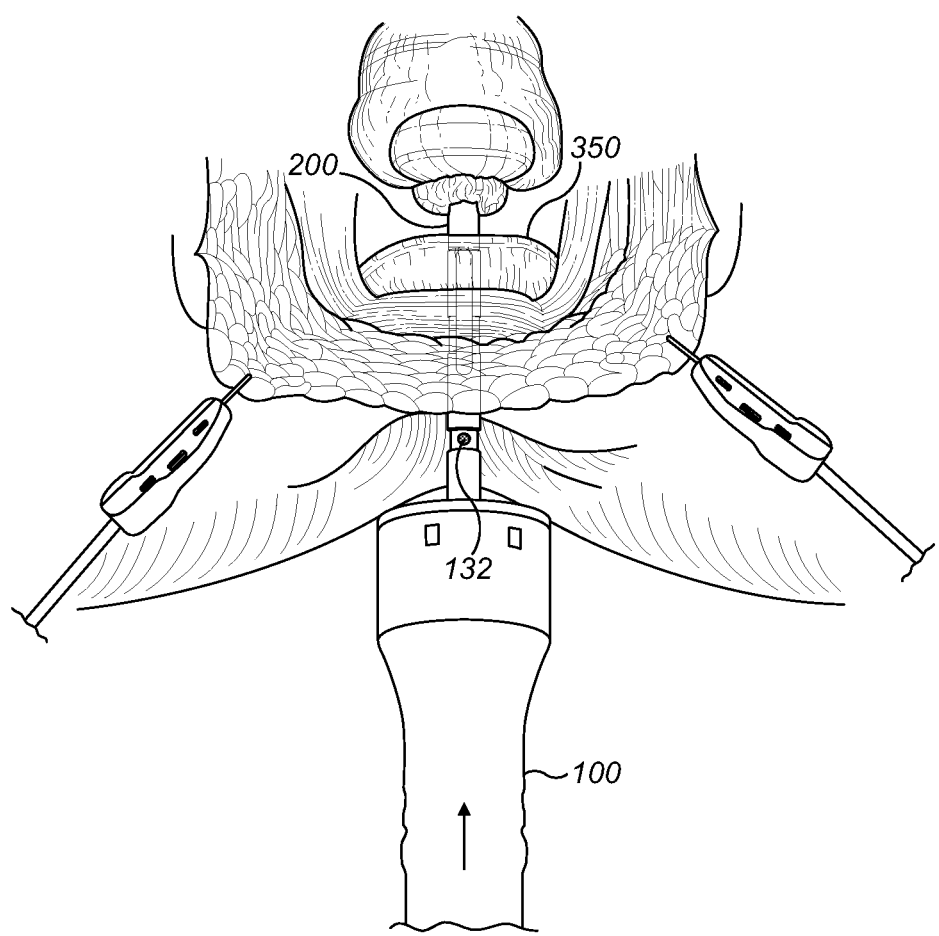
FIGS. 31a and 31b shows the anvil 200 and stapler 100 fully docked. An anvil docking indicator 132 is visible through a viewing window present on the anvil shaft.
Figure 31B:
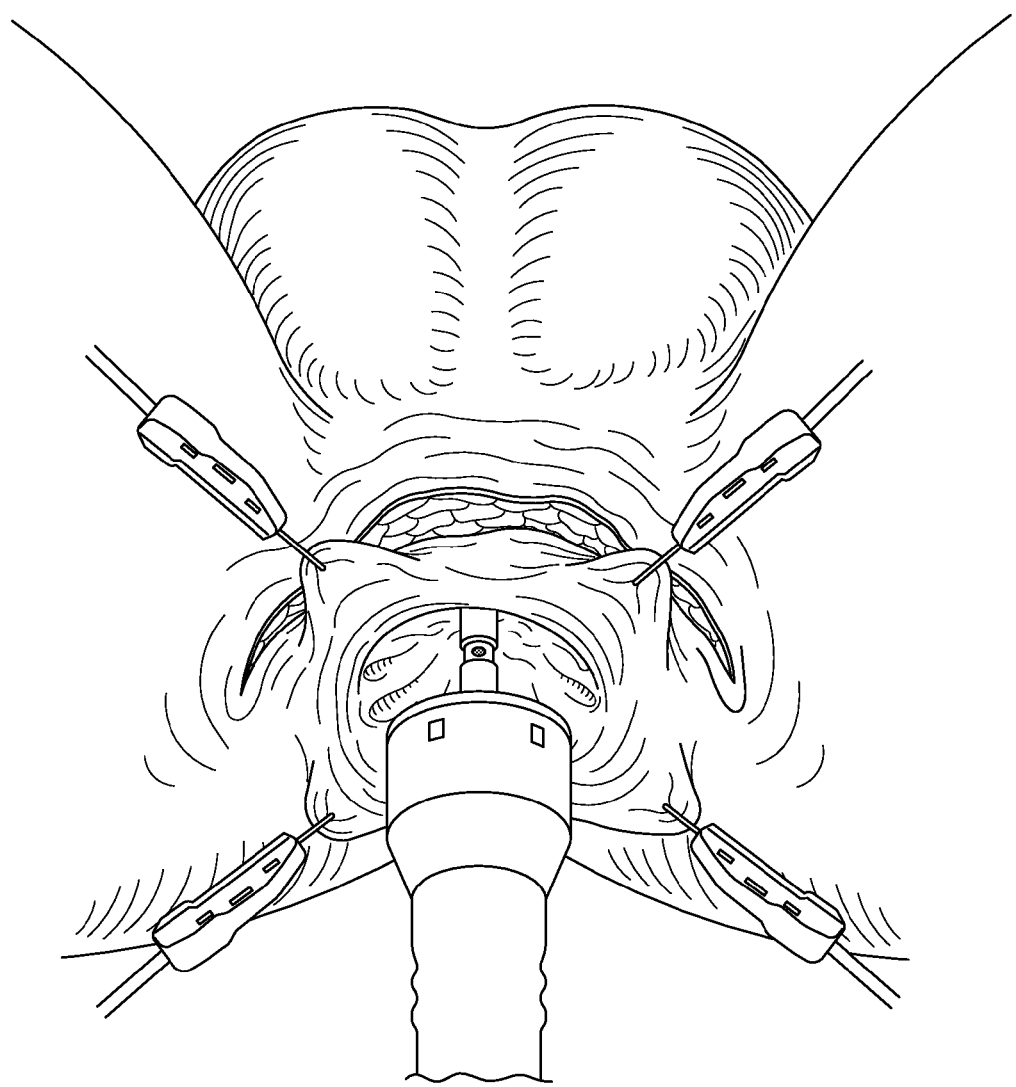

FIGS. 30a and 30b show the anvil fully retrieved through the distal stump enterotomy and fully externalised in preparation for endo-anal or extracorporeal docking of the anvil shaft and stapler. The anvil tongs 370 have been repositioned to grasp the anvil to stabilise and facilitate docking FIGS. 30a and 30b clearly show the docking indicator on the anvil docking pin and the viewing window on the anvil shaft through which the docking indicator will be visible to confirm docking has been completed FIGS. 31a and 31b show the anvil and anvil docking pin fully docked with the docking indicator clearly in view through the viewing window. The stapler device is then closed by activation of the trigger to draw the two tissues together such that the staple body housing passes endoanally into the anorectal stump, taking care to traverse the sphincter mechanism and the full length of the anorectal stump 350. When the anvil and stapler housing are suitably positioned, the stapling means is actuated to create the anastomosis Conventional docking occurs above the level of the staple housing. However the stapler with an elongated anvil shaft allows for virtually unlimited extension of the anvil docking pin-anvil shaft assembly to allow for anatomical variances, such as obese patients, and for additional procedures, for example bariatric surgery procedures where externalisation of coupling of staple anvil assembly to stapler is desirable.

In a fourth aspect of the invention, there is provided a method of forming or creating a stoma trephine in a subject using the kit of parts of the invention, comprising:

forming an incision in a tissue where a stoma is to be formed;

inserting the anvil 200 of the stapler apparatus into the subject;

grasping the anvil shaft 240 with a forceps 2;

docking the anvil shaft 240 onto the anvil docking pin 130 of the stapler 100; and activating the trigger 112 to dispense a series of staples in the tissue being stapled.

The method of forming or creating a stoma may further comprise the step of retrieving the anvil shaft through the incision using the forceps. The forceps may be used to manipulate the anvil shaft to maneuver the anvil shaft and retrieve it past the staple line in the tissue where the stoma trephine is to be formed. The anvil head may be attached to an organ or section of tissue, for example a section of intestine or skin, such that the anvil head is contained within the lumen of the organ and the anvil shaft projects out of the tissue. The anvil shaft is then ready for engagement with an anvil docking pin. Therefore, methods of the invention can include the step of attaching the anvil via the anvil head to an organ or tissue, for example by means of a purse string suture.

In another embodiment of the invention, the method may comprise applying one or more mesh reinforcements to the anvil docking pin or anvil shaft.

As for the method of forming an anastomoses, the mesh or meshes may be arranged in any order, so that they are above or below the tissue being stapled or, where a plurality of tissues layers are being stapled together, the meshes may be positioned between the tissue layers. If a mesh or meshes are used, the circular blade of the stapler apparatus will cut the mesh to ensure a continuous lumen between the interior of the organ in which the stoma trephine is being formed and the exterior of the organ. Suturing of the outer rim of the mesh or meshes may be required to fully secure the meshes in position.

In yet another embodiment of the invention, the method of forming a stoma trephine may further comprise the step of operating the retracting means of the stapler to retract the anvil docking pin and engaged anvil into the stapler.

Manipulation or positioning of the anvil during the procedure may involve the use of the forceps 2 and/or the tongs 370.

Actuation of the stapling means by activation of the trigger 112 causes the staples to be dispensed and to fix together the tissue disposed at the interface between the anvil head and stapling means. Advancement of the circular blade along the longitudinal axis causes formation of the trephine between, for example, an internal cavity (such as the abdominal cavity) and the exterior of the body. The dispensed deformed staples secure the perimeter of the trephine by securing together layers of tissue.

The forceps of the invention is depicted in use for creating a stoma trephine in FIGS. 16 to 24.

Figure 16:
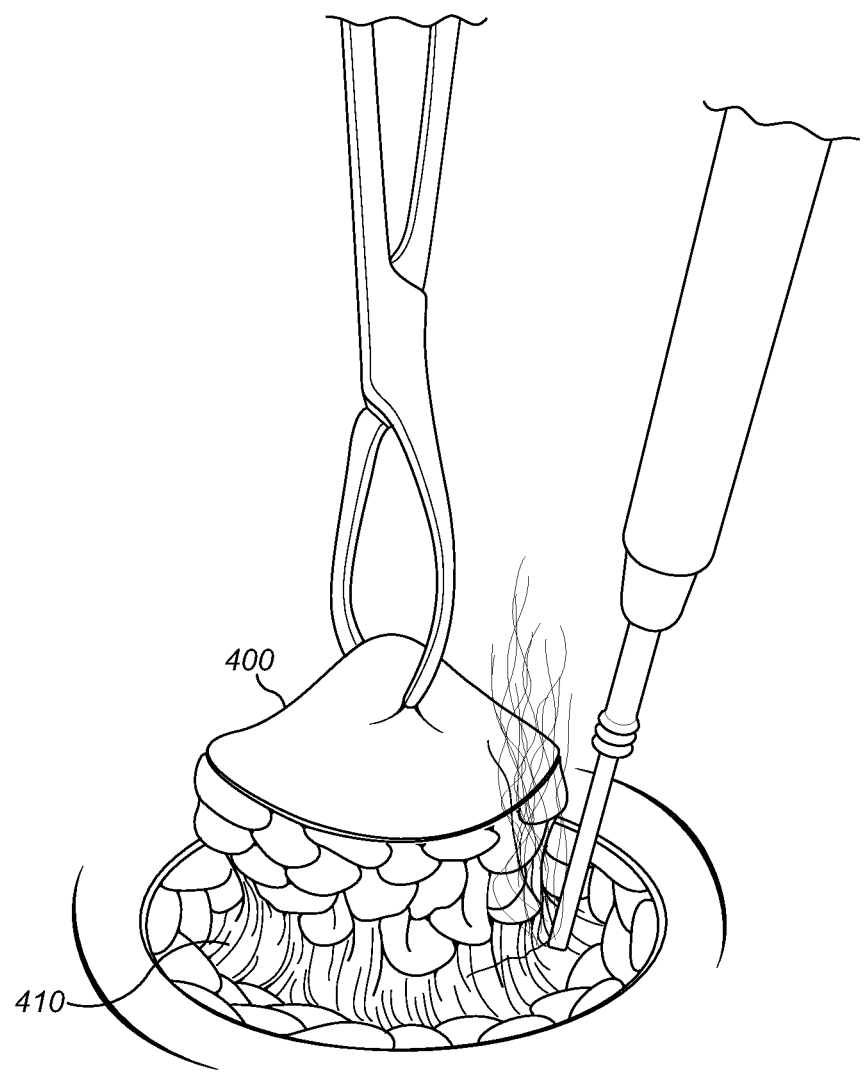
FIG. 16 shows the excision of a cylinder of abdominal wall skin and subcutaneous tissue 400 down to the rectus sheath 410 at the site at which a stoma trephine is to be formed.
Figure 17:
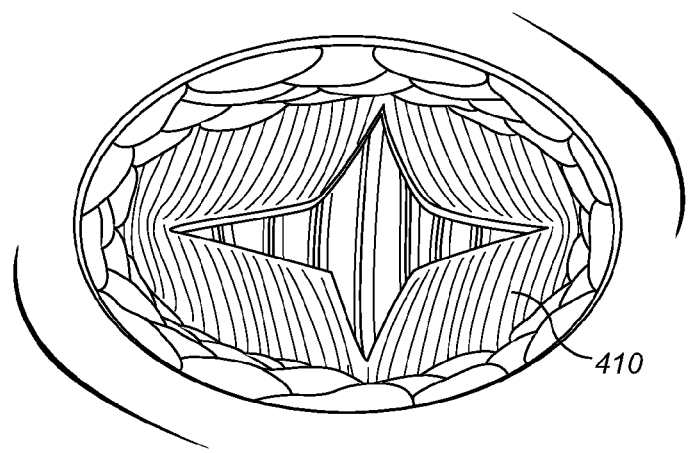
FIG. 17 show the rectus sheath 410 opened with a cruciate incision.
Figure 18:
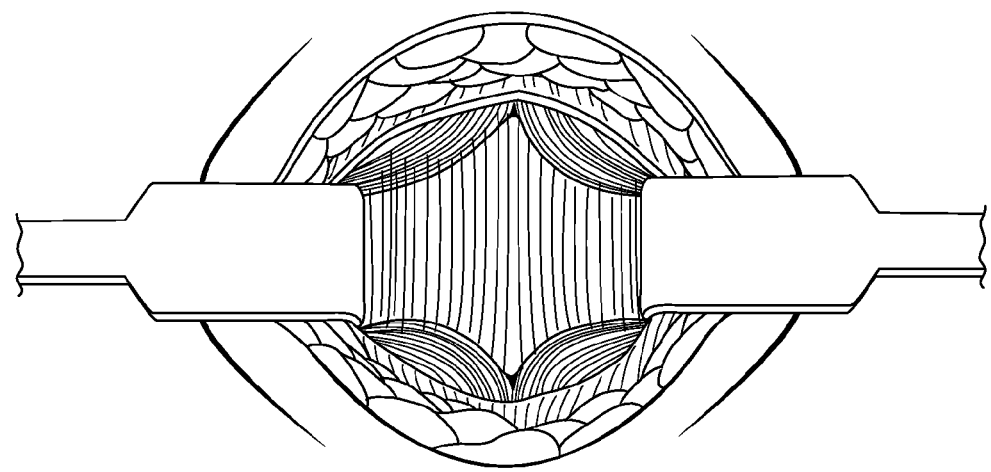
FIG. 18 shows the incision being held open using retractors (Langenbeck retractors).

Formation of stomas (and stoma trephines) in open surgery generally commence by excising a cylinder of abdominal wall skin and subcutaneous tissue 400 down to the rectus sheath 410, as shown in FIG. 16. The sheath 410 is then opened with a cruciate incision and the rectus muscle split in the line of its fibres (FIG. 17) and optionally held open using retractors (FIG. 18). An anvil 200 of an appropriate size is then introduced via the open abdomen. The diameter of the stapler and anvil depends on the diameter of the bowel which will eventually traverse the stoma trephine.

Figure 19:
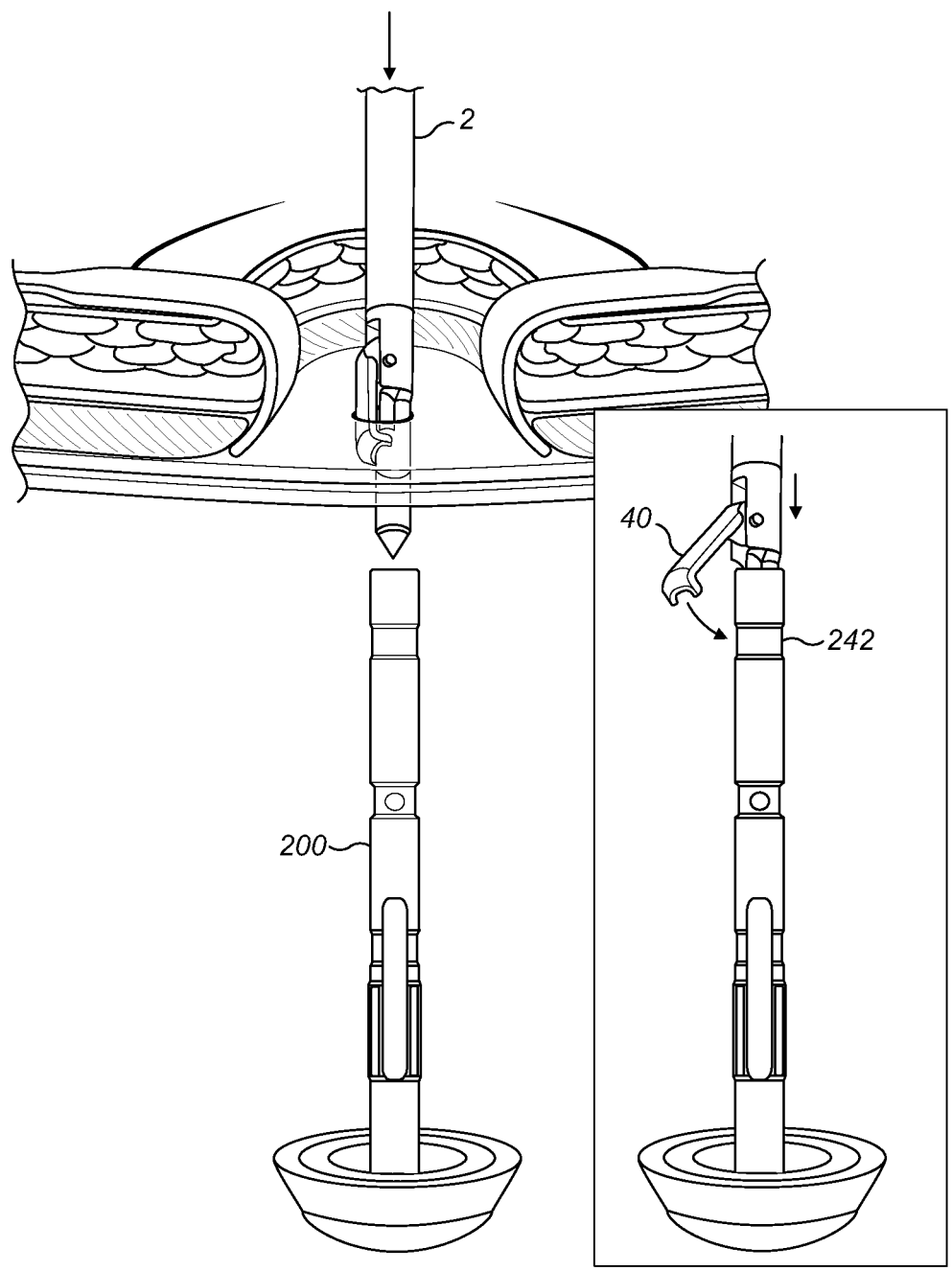
FIG. 19 shows a forceps 2 of the current invention being used to retrieve an anvil 200 from inside a body cavity.
Figure 20:
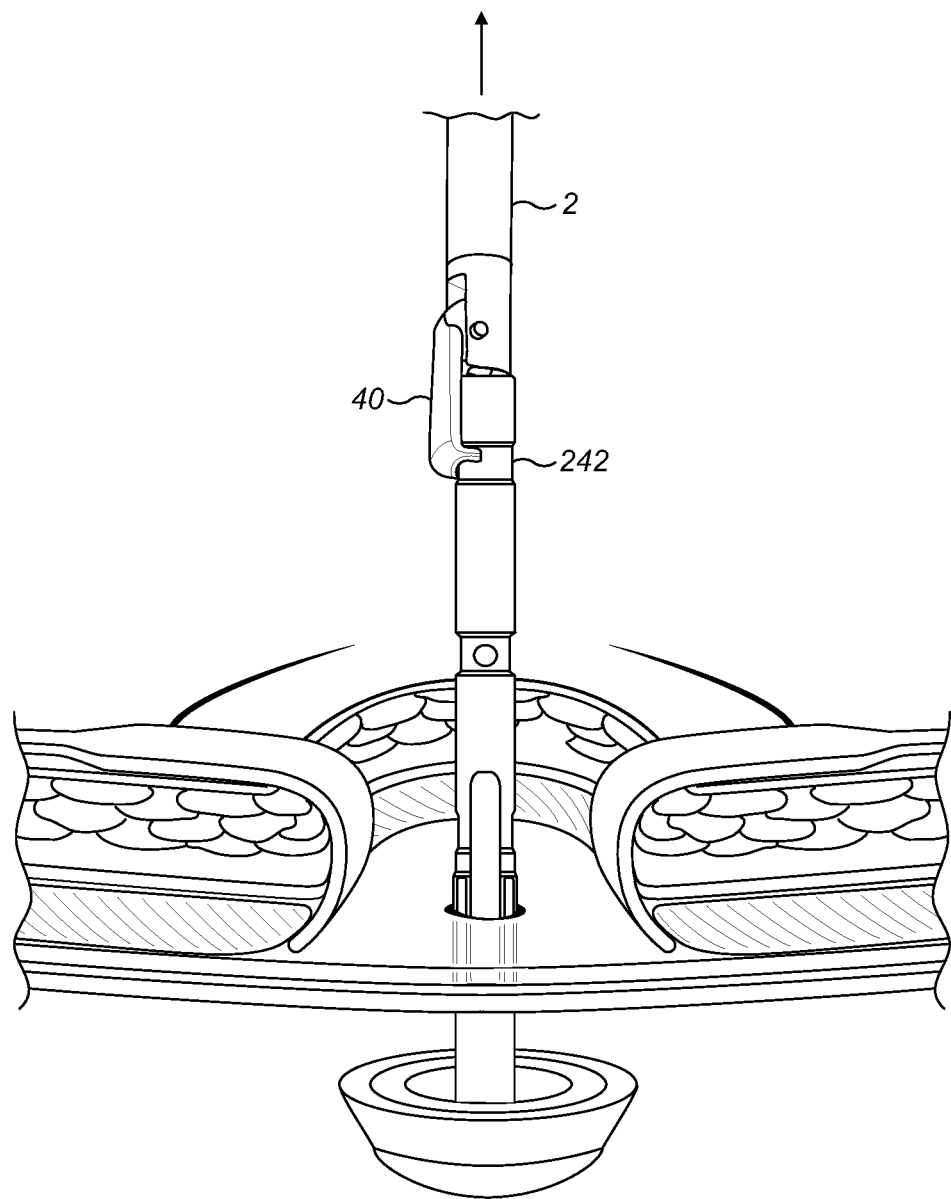
FIG. 20 shows the anvil shaft exteriorised using the forceps 2 of the invention.

The forceps 2 of the invention are then inserted via the abdominal wall trephine to penetrate the posterior rectus sheath and peritoneum (FIG. 19). The forceps is sufficiently sharp to penetrate the layers it needs to transgress. The forceps is used to grasp the anvil shaft and withdraw the anvil shaft through the incision to exteriorize the anvil shaft through the trephine to emerge on the abdominal wall (FIG. 20). The tooth of the movable grasper is located to align with the indentations on the anvil shaft to provide a more secure connection between the forceps and the anvil and also to maintain a narrow profile of the trocar tip of the forceps, even when engaged with an anvil shaft.

Figure 21:
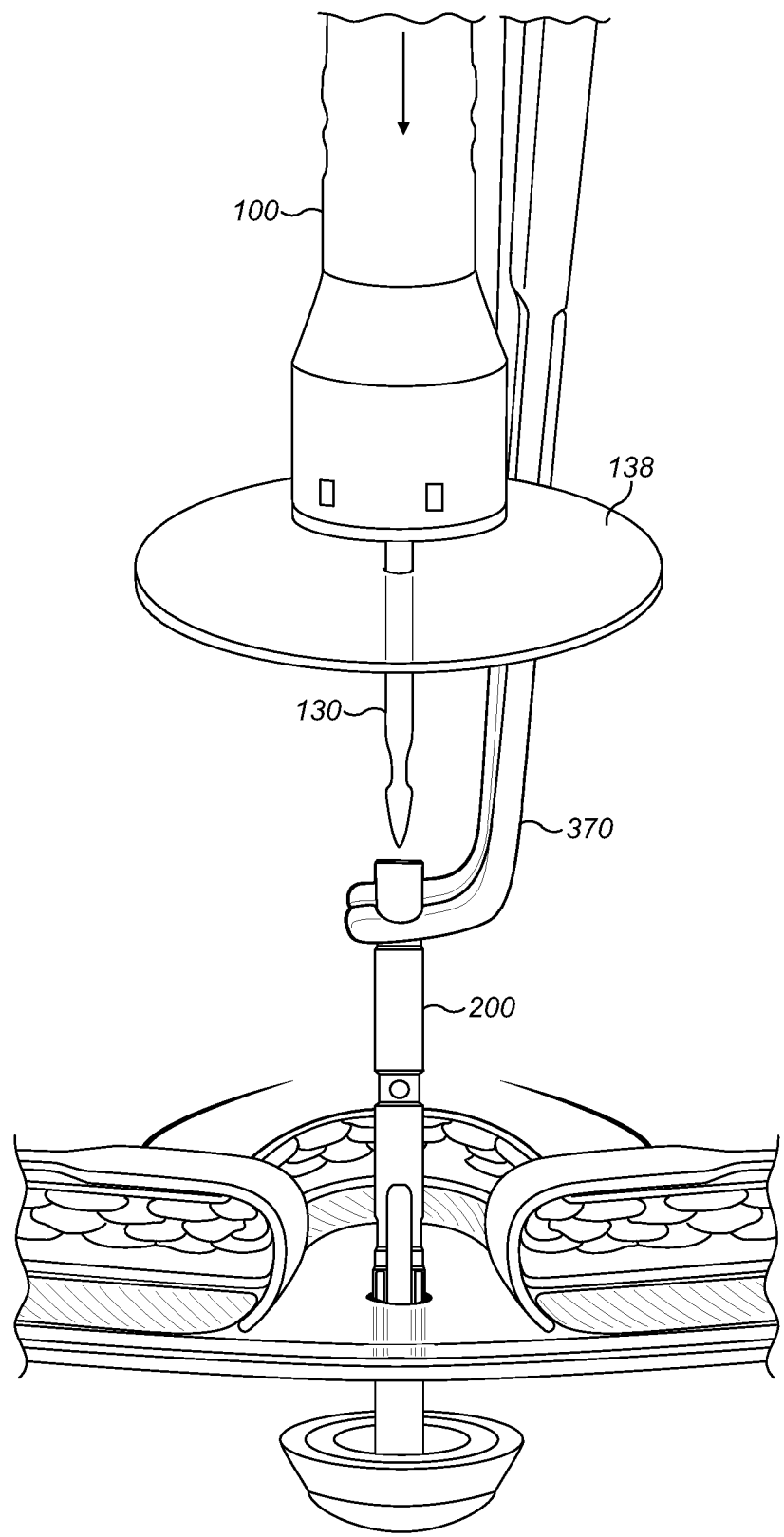
FIG. 21 shows a surgical stapler 100 of the kit of the invention with mesh reinforcement 138 applied to the anvil docking pin 130 and the anvil 200 aligned with the anvil docking pin ready for engagement. The anvil is being steadied using tongs 370.

The tongs 370 are optionally used externally to grasp the anvil shaft and steady it and facilitate eventual mating of the anvil shaft with the anvil docking pin emanating from the stapling means (FIG. 21). A mesh 138 which is optionally configured in a circular design with a diameter greater than or equal to that of the anvil can optionally be prepared by creating a small defect in its centre. The defect in the mesh can then be utilised to insert the mesh onto the anvil docking pin 130, as show in FIG. 21.

Figure 22:
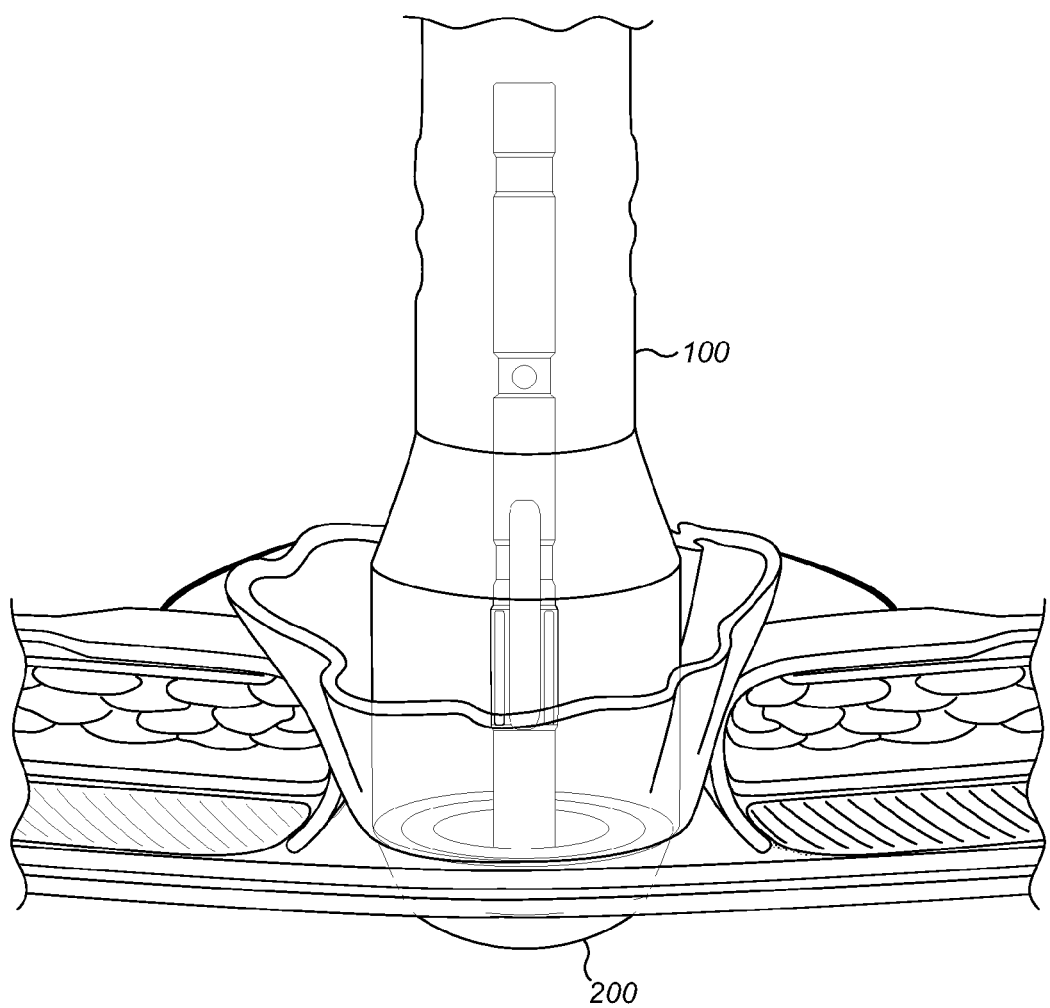
FIG. 22 shows the anvil 200 and stapler 100 fully engaged and the anvil retracted into the stapler.
Figure 23:
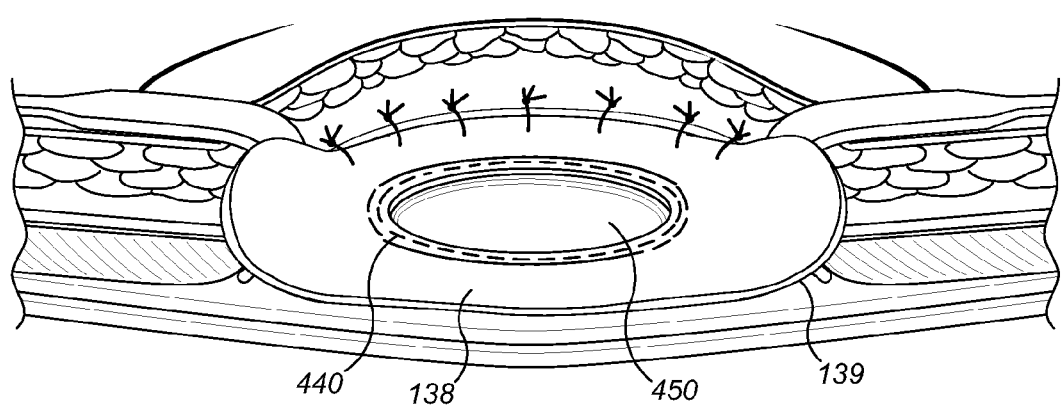
FIG. 23 shows the row of staples 440 defining a stoma trephine 450 after actuation of the stapler and subsequent suturing of the loose rim 139 of the mesh 138.

The anvil shaft is grasped by the tongs 370 and mated with the anvil docking pin 130 of the stapler. Once successful locking has been achieved the retracting means is operated to enclose the mesh, the posterior rectus sheath and the peritoneum at the interface between the anvil head and the stapling means (FIG. 22). The trigger is then activated to actuate the stapling means before removing the stapler 100, taking with it a disc of mesh, posterior rectus sheath and peritoneum and leaving a precise reinforced stapled trephine 450 defined by a staple line 440. The rim 139 of the mesh 138 is next optionally sutured to the anterior rectus sheath with interrupted 0 PDS (polydioxanone) sutures or stapled so it lies flat against the anterior sheath and totally lines the trephine 450 through the split muscle fibres (FIG. 23).

Figure 24:
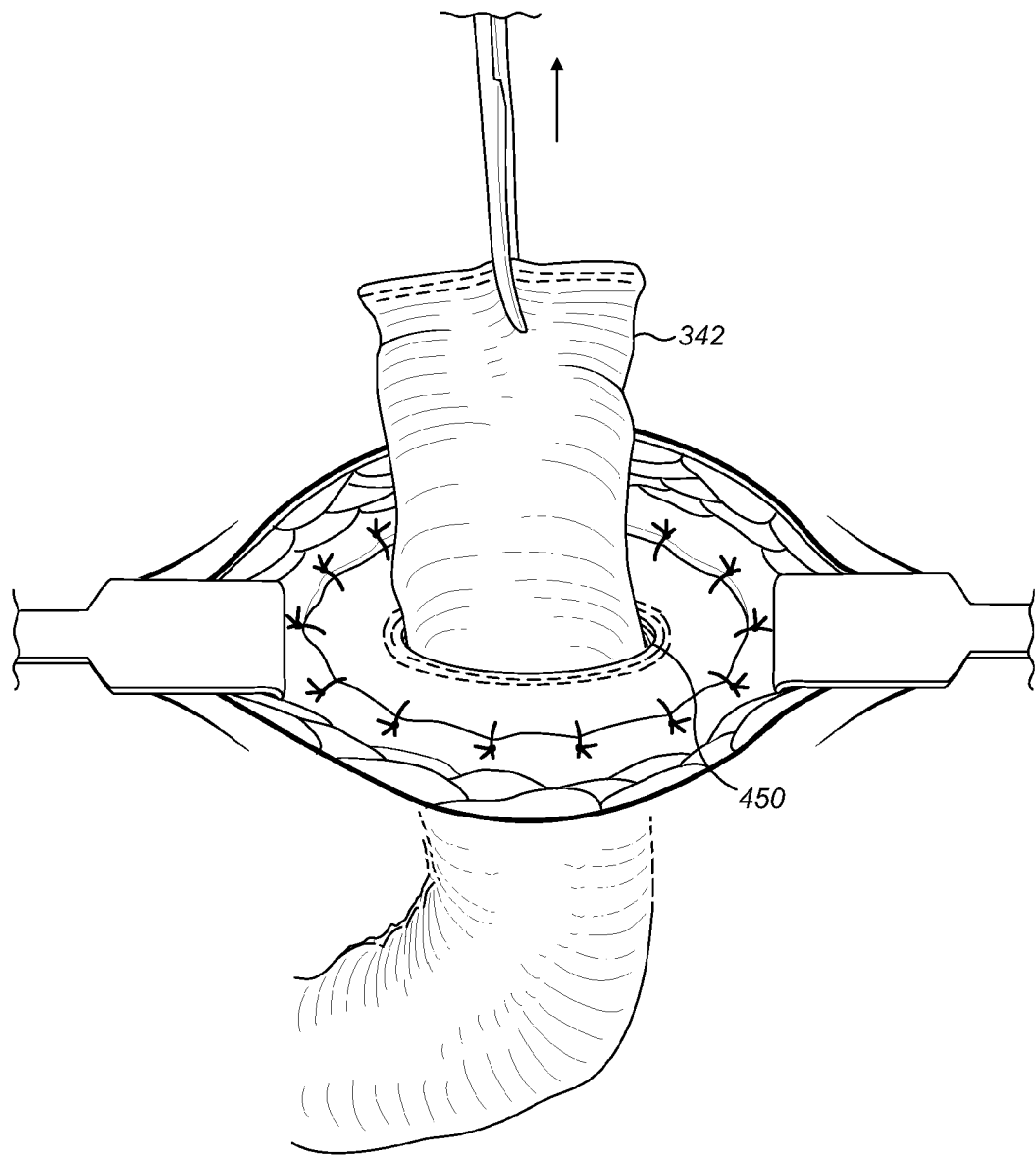
FIG. 24 shows a section of bowel 342 being retrieved through the newly created stoma trephine 450.

The colon or ileum is then drawn through the trephine and the stoma is fashioned in the usual way (FIG. 24; a description of the formation of stomas is provided in, for example, Keighley, M. R. B. & Williams, N. S., "Surgery of the Anus Rectum and Colon", 3rd Ed., Saunders Ltd., 2008: Chapter 5, pp. 175-278).

This technique incorporating a reinforcing mesh has been developed by the present inventors and is referred to as SMART (Stapled Mesh stomA Reinforcement Technique). Previous studies that have incorporated a mesh were conducted at open surgery and the mesh is placed sub-peritoneally via an abdominal approach. Although such a technique is relatively simple it markedly increase operating time and is difficult to perform laparoscopically. The SMART technique using a forceps and stapler apparatus of the invention is simple and quick to perform, and it places the mesh in the correct layer of the abdominal wall so as to prevent adhesions. This technique is reproducible and can be performed both at open and laparoscopic surgery with ease. The stapler allows the creation of a stoma trephine and simultaneously reinforces it with a mesh. It can be used for the formation of virtually any kind of stoma, including in ileostomy and colostomy construction. The forceps allow easy and quick manipulation of the stapler anvil, in particular in laparoscopic techniques since the trocar tip can be used to pierce the tissues and retrieve the stapler anvil without over stretching the stoma trephine (over stretching the stoma trephine can lead to parastomal herniation).

The methods of the invention can be used with any forceps of kit of parts according to the invention. For example, the anvil may comprise one or more hollow channels that extend from the anvil shaft through the entire thickness of the anvil head. This allows the anvil or stapler to be attached to a suction device. The apparatus can then be used to manipulate tissue during the procedure by creating a vacuum at the apertures in the surface of the anvil head.

Use of an anvil 245 with one or a plurality of hollow channels and the suction modification described above and as shown in FIGS. 25 to 27 helps to ensure the bowel that will constitute the stoma can be withdrawn easily through the trephine and be correctly orientated. This maneuver is especially difficult in laparoscopic stoma formation, due to restricted access to the abdominal cavity in such procedures.

The stapling and forceps can be used in open, endoscopic and laparoscopic surgical procedures and methods, although the forceps 2 of the invention are especially suited to laparoscopic procedures. The anastomosis or stoma trephine may be formed in any desirable surface or biological tissue in a patient or subject that is capable of being stapled. Suitable biological tissues include organ walls, the endoderm, ectoderm, mesoderm, the alimentary canal, small intestine, large intestine, duodenum, jejunum, ileum, cecum, colon, rectum, connective tissue, muscle tissue, epithelial tissue, stomach, oesophagus, trachea, peritoneum, rectus sheath, distal rectal stump, endothelium, gut endothelium, skin and the abdominal wall. Anastomoses or stoma trephines may be formed between two or more of theses biological tissues. For anastomoses, both tissues generally have lumens which are joined together in forming the anastomosis. For example, an anastomosis may be formed between two pieces of bowel or between the intestine and a distal rectal stump of a patient. Such anastomoses are also known as end-to-end anastomoses. The stoma trephine may be formed in the abdomen of a patient or in any desired place where a stoma trephine is to be formed.

The surfaces or tissues to be stapled include biological tissues such as the bowel or intestinal wall, the wall of the oesophagus, the posterior rectus sheath, a distal rectal stump or the peritoneum. Other tissues include the external tissues of the body, for example the skin when creating stomas, or organs generally. The tissues to be stapled may also be referred to as surfaces or materials to be stapled.

The methods can be carried out in vivo in patients (either human or non-human patients). The methods can also be ex vivo methods carried out on tissue samples.

The methods involving the forceps of the invention an employ any surgical stapler apparatus suitable for use in such methods. For example, the forceps can be used with the Chex™ CS-28 Curved Single Use Intraluminal Stapler (available from Frankenman International Limited).

If the methods employ an anvil 245 comprising one or more hollow channels that extend from the anvil shaft through the entire thickness of the anvil head, the methods may additionally comprise a step of applying suction through the anvil to manipulate the surface or tissue to be stapled. The manipulation of the tissue or surface to be stapled in this way allows it to be positioned appropriately to facilitate formation of the anastomosis or stoma.

In a fifth aspect of the invention, there is provided the use of the forceps of the invention in the formation of an anastomosis or stoma trephine.

In a sixth aspect of the invention, there is provided the use of a kit of parts of the invention in the formation of an anastomosis or stoma trephine.

Features of the second and subsequent aspects of the invention are as for the first aspect of the invention, mutatis mutandis.

EXAMPLES

The invention will now be further described with reference to the following examples which are presented merely for illustrative purposes and are not intended to be limiting on the scope of the invention.

Example 1

Anterior Perineal PlanE for Ultra-Low Anterior Resection of the Rectum (the APPEAR Technique)

Fourteen patients were enrolled, 7 with neoplasia, 5 with ulcerative colitis, and 2 with traumatic rectal damage. Patients were evaluated preoperatively, and at a median of 2 years after surgery.

Nine of 14 patients underwent ileostomy reversal and were followed up for a minimum of 1 year, with 1 patient awaiting closure. Four patients had not yet been considered for ileostomy reversal due to anastomotic perineal fistulae. Transient sexual dysfunction was noted in 3 of 14 patients, but no urological problems occurred.

When the APPEAR procedure was performed for neoplasia or trauma, postoperative median Wexner continence score was 5 (range 0-8, n=6), with a median defecation frequency of 3 (range 1-8/day). All cancers were completely excised with no local recurrence. Following APPEAR with restorative proctocolectomy for ulcerative colitis, median Wexner continence score was 2 (range 0-6, n=3), with a median daily defecatory frequency of 3 (range 1-5). Preoperative SF-36 scores (36-part short form questionnaire that measures quality of life) did not change significantly following ileostomy closure, and anorectal physiological testing was unaltered following perineal dissection.

The APPEAR procedure therefore provides an alternative technique to effect an ultra-low sphincter-saving anastomosis, when this is not possible by conventional surgery. This is a promising new procedure with the potential to reduce the need for a permanent stoma even further than is currently the case. The use of a stapler apparatus described herein in procedures such as the APPEAR technique allows endo-anal or extracorporeal docking of the anvil and stapler, allowing the surgeon to see more clearly where the anvil is to aid docking onto the anvil docking pin. The elongated shaft also allows the surgeon to see extracorporeally that the anvil has fully engaged with the stapler.

Example 2

Stapled Mesh StomA Reinforcement Technique (SMART)

Parastomal hernias (PH) are frequent with a high morbidity. Three randomised controlled trials showed that mesh reinforcement significantly reduced their incidence. The techniques however were time consuming, difficult to perform laparoscopically and relied on manual stretching of the trephine. SMART obviates these problems.

SMART uses the stapler apparatus described herein to create a precise trephine in the posterior rectus sheath and peritoneum and simultaneously fixes mesh subperitoneally and circumferentially to the trephine. Stretching is minimised. 9 patients (M:F 2:7, median age 55 yrs range 24-77) at high risk of PH and in whom randomisation in a controlled trial was contraindicated underwent SMART (7 open: 2 laparoscopic).

There was no post-operative (30 days) morbidity related to stoma formation. All stomas functioned satisfactorily within 48 hours. One patient developed intestinal obstruction after hospital discharge unrelated to stoma formation and another developed temporary peristomal pain and swelling following successful cardiorespiratory resuscitation. During follow-up of 13 weeks (2-14), no parastomal hernia was found.

SMART is a new and simple means of precisely creating a reinforced stoma trephine at both open and laparoscopic surgery and it reduces the parastomal herniation rate. The forceps of the present invention can be used in the SMART or APPEAR techniques to assist in manipulation of the anvil, as described above.

The invention claimed is:

1. A kit of parts comprising a forceps and a stapler apparatus, the stapler apparatus comprising:
   (a) a stapler having a proximal end, a distal end and a longitudinal axis, the stapler further comprising
      (i) a trigger;
      (ii) an anvil docking pin aligned substantially parallel with the longitudinal axis of the stapler; and
      (iii) a stapling means, the anvil docking pin and stapling means being at the distal end of the stapler; and
   (b) a detachable anvil, comprising an anvil head and an anvil shaft,
   wherein the anvil shaft is adapted to receive the anvil docking pin and operation of the trigger causes the stapling means to be actuated,
   wherein the trocar of the forceps is adapted for insertion into the anvil shaft; and
   the forceps comprising:
      (a) an elongate body;
      (b) a grip region at end of the elongate body, the grip region comprising a lever;
      (c) a grasping assembly at the opposite end of the elongate body, the grasping assembly comprising a moveable grasper and a trocar; and
      (d) an actuating mechanism coupling the lever to the grasping assembly for effecting movement of the grasper relative to the elongate body.

2. The kit of parts of claim 1, wherein the length of the anvil shaft is between 4 and 20 cm.

3. The kit of parts of claim 1, wherein the grasper of the forceps comprises a tooth and the anvil shaft comprises an indentation, and wherein the tooth is adapted for engagement with the indentation.

4. The kit of parts of claim 1 further comprising a safety guard.

5. The kit of parts of claim 1 further comprising a mesh.

* * * * *